(12) United States Patent
Gao et al.

(10) Patent No.: US 7,544,638 B2
(45) Date of Patent: *Jun. 9, 2009

(54) DEVICE FOR CHEMICAL AND BIOCHEMICAL REACTIONS USING PHOTO-GENERATED REAGENTS

(75) Inventors: Xiaolian Gao, Houston, TX (US); Xiaochuan Zhou, Houston, TX (US); Erdogan Gulari, Ann Arbor, MI (US)

(73) Assignees: The Regents of the University of Michigan, Ann Arbor, MI (US); University of Houston, Houston, TX (US)

( * ) Notice: Subject to any disclaimer, the term of this patent is extended or adjusted under 35 U.S.C. 154(b) by 582 days.

This patent is subject to a terminal disclaimer.

(21) Appl. No.: 10/340,928

(22) Filed: Jan. 13, 2003

(65) Prior Publication Data

US 2008/0318806 A1  Dec. 25, 2008

Related U.S. Application Data

(63) Continuation of application No. 10/241,411, filed on Sep. 11, 2002, which is a continuation of application No. 10/157,442, filed on May 29, 2002, which is a continuation of application No. 09/248,093, filed on Feb. 10, 1999, now Pat. No. 6,426,184.

(60) Provisional application No. 60/074,368, filed on Feb. 11, 1998.

(51) Int. Cl.
*C40B 50/08* (2006.01)

(52) U.S. Cl. ............................ 506/27; 435/6; 506/23; 506/33

(58) Field of Classification Search .............. 435/4, 435/6, 7.1, 283.1, 286.1, 286.2, 287.1, 287.2, 435/288.3; 436/94, 145, 518, 523, 524, 527, 436/528, 72, 805, 91; 422/129, 131; 530/334
See application file for complete search history.

(56) References Cited

U.S. PATENT DOCUMENTS

| | | | |
|---|---|---|---|
| 4,146,329 A | 3/1979 | King et al. | 356/152 |
| 4,163,150 A | 7/1979 | Stankewitz | 250/205 |
| 4,301,363 A | 11/1981 | Suzuki et al. | 250/216 |
| 4,367,251 A | 1/1983 | Crivello | |
| 4,571,603 A | 2/1986 | Hornbeck et al. | 346/160 |
| 4,596,992 A | 6/1986 | Hornbeck | 346/76 |
| 4,615,595 A | 10/1986 | Hornbeck | 353/122 |
| 4,662,746 A | 5/1987 | Hornbeck | 350/269 |
| 4,719,615 A | 1/1988 | Feyrer | |
| 5,028,939 A | 7/1991 | Hornbeck et al. | 346/160 |
| 5,096,279 A | 3/1992 | Hornbeck et al. | 359/230 |
| 5,143,854 A * | 9/1992 | Pirrung et al. | 436/518 |
| 5,158,855 A | 10/1992 | Sugiyama et al. | 430/192 |
| 5,202,231 A | 4/1993 | Drmanac et al. | 435/6 |
| 5,247,180 A | 9/1993 | Mitcham et al. | 250/492.1 |
| 5,252,743 A | 10/1993 | Barrett et al. | 548/303.7 |
| 5,318,679 A | 6/1994 | Nishioka | 204/157.68 |
| 5,324,483 A | 6/1994 | Cody et al. | 422/131 |
| 5,384,261 A | 1/1995 | Winkler et al. | 436/518 |
| 5,393,877 A | 2/1995 | McLean | |
| 5,401,607 A | 3/1995 | Takiff et al. | 430/253 |
| 5,401,837 A | 3/1995 | Nelson | |
| 5,405,783 A | 4/1995 | Pirrung et al. | 436/518 |
| 5,412,087 A | 5/1995 | McGall et al. | 536/24.3 |
| 5,424,186 A * | 6/1995 | Fodor et al. | 435/6 |
| 5,445,934 A | 8/1995 | Fodor et al. | 435/6 |
| 5,451,683 A | 9/1995 | Barrett et al. | 548/302.7 |
| 5,474,796 A | 12/1995 | Brennan et al. | 427/2.13 |
| 5,482,867 A | 1/1996 | Barrett et al. | 436/518 |
| 5,489,678 A | 2/1996 | Fodor et al. | 536/22.1 |
| 5,504,614 A | 4/1996 | Webb et al. | 359/223 |
| 5,510,270 A | 4/1996 | Fodor et al. | 436/518 |
| 5,517,280 A | 5/1996 | Quate | 355/71 |
| 5,535,047 A | 7/1996 | Hornbeck | 359/295 |

(Continued)

FOREIGN PATENT DOCUMENTS

DE    692 18 572 T2    7/1993

(Continued)

OTHER PUBLICATIONS

Sampsell, Jeffrey B., "Digital micromirror device and its application to projection displays", 1994, J. Vac. Sci. Technol. B, 12(6), pp. 3242-3246.*

(Continued)

*Primary Examiner*—J D Schultz
*Assistant Examiner*—Jeffrey S. Lundgren
(74) *Attorney, Agent, or Firm*—Casimir Jones S.C.

(57) ABSTRACT

This invention provides method and apparatus for performing chemical and biochemical reactions in solution using in situ generated photo-products as reagent or co-reagent. In particular, the present invention provides methods and devices for generating a photogenerated reaction in solution on a substrate comprising generating a light beam using an optical device system comprising a light source and a computer-controlled spatial optical modulator comprising a digital micromirror device and using the spatial optical modulator to direct light to fluidly isolated reaction sites under conditions such that a photogenerated reaction takes place. The method and apparatus of the present invention have applications in parallel synthesis of molecular sequence arrays on solid surfaces.

22 Claims, 26 Drawing Sheets

U.S. PATENT DOCUMENTS

| | | | |
|---|---|---|---|
| 5,539,567 A | 7/1996 | Lin et al. | 359/281 |
| 5,539,568 A | 7/1996 | Lin et al. | 359/285 |
| 5,552,471 A | 9/1996 | Woo | |
| 5,556,752 A | 9/1996 | Lockhart et al. | 435/6 |
| 5,571,639 A * | 11/1996 | Hubbell et al. | 435/6 |
| 5,578,832 A | 11/1996 | Trulson et al. | 250/458.1 |
| 5,583,688 A | 12/1996 | Hornbeck | 359/291 |
| 5,585,481 A | 12/1996 | Arnold, Jr. | |
| 5,593,839 A | 1/1997 | Hubbell et al. | 435/6 |
| 5,599,695 A | 2/1997 | Pease et al. | 435/91.1 |
| 5,600,383 A | 2/1997 | Hornbeck | 348/771 |
| 5,623,049 A | 4/1997 | LobberDing | |
| 5,625,052 A | 4/1997 | Woo | |
| 5,631,734 A | 5/1997 | Stern et al. | 356/317 |
| 5,653,939 A * | 8/1997 | Hollis et al. | 422/50 |
| 5,656,741 A | 8/1997 | Chow | |
| 5,656,744 A | 8/1997 | Arnold, Jr. | |
| 5,666,190 A | 9/1997 | Quate et al. | 355/71 |
| 5,677,195 A | 10/1997 | Winkler et al. | 436/518 |
| 5,695,940 A | 12/1997 | Drmanac et al. | 435/6 |
| 5,738,829 A | 4/1998 | Kempe | |
| 5,744,305 A | 4/1998 | Fodor et al. | 435/6 |
| 5,750,672 A | 5/1998 | Kempe | |
| 5,753,788 A | 5/1998 | Fodor et al. | 536/22.1 |
| 5,768,009 A | 6/1998 | Little | 359/293 |
| 5,831,070 A | 11/1998 | Pease et al. | 536/25.3 |
| 5,835,256 A | 11/1998 | Huibers | 359/291 |
| 5,837,832 A | 11/1998 | Chee | |
| 5,869,696 A | 2/1999 | Reddy et al. | |
| 5,883,705 A | 3/1999 | Minne et al. | 355/71 |
| 5,919,523 A | 7/1999 | Sundberg | |
| 5,936,759 A | 8/1999 | Buttner | 359/291 |
| 5,953,153 A | 9/1999 | Conner et al. | 359/298 |
| 5,958,268 A | 9/1999 | Engelsberg | |
| 5,959,098 A | 9/1999 | Goldberg | |
| 5,991,066 A | 11/1999 | Robinson | |
| 6,005,125 A | 12/1999 | Zhang | |
| 6,015,895 A | 1/2000 | Pon | |
| 6,031,091 A | 2/2000 | Arnold, Jr. | |
| 6,043,353 A | 3/2000 | Pon | |
| 6,051,374 A | 4/2000 | Simons | |
| 6,083,697 A * | 7/2000 | Beecher et al. | 435/6 |
| 6,090,934 A | 7/2000 | Kumar et al. | |
| 6,210,878 B1 | 4/2001 | Pinkel | |
| 6,215,579 B1 | 4/2001 | Bloom et al. | 359/298 |
| 6,271,957 B1 * | 8/2001 | Quate et al. | 359/298 |
| 6,295,153 B1 | 9/2001 | Garner | 359/212 |
| 6,375,903 B1 * | 4/2002 | Cerrina et al. | 422/131 |
| 6,426,184 B1 * | 7/2002 | Gao et al. | 435/6 |
| 6,465,175 B2 | 10/2002 | Horn et al. | |
| 6,480,324 B2 | 11/2002 | Quate et al. | 359/298 |
| 6,542,241 B1 | 4/2003 | Thorwirth | |
| 2003/0138363 A1 * | 7/2003 | Gao et al. | 422/186 |
| 2003/0143131 A1 * | 7/2003 | Gao et al. | 422/186 |
| 2003/0186226 A1 | 10/2003 | Brennan | |
| 2003/0186427 A1 | 10/2003 | Gao | |
| 2004/0023368 A1 | 2/2004 | Gao | |

FOREIGN PATENT DOCUMENTS

| | | |
|---|---|---|
| EP | 0 537 524 A1 | 4/1993 |
| EP | 0 961 174 | 12/1999 |
| WO | WO 93/02992 | 2/1993 |
| WO | WO 93/09668 | 5/1993 |
| WO | WO 93/22678 | 11/1993 |
| WO | WO 96/11878 | 4/1996 |
| WO | WO 97/26569 | 7/1997 |
| WO | WO 97/39151 | 10/1997 |
| WO | WO 98/20967 | 5/1998 |
| WO | 99/41007 | 8/1998 |
| WO | WO 99/42813 | 8/1999 |
| WO | WO 99/63385 | 12/1999 |
| WO | 00/12524 | 3/2000 |
| WO | WO 00/13017 | 3/2000 |
| WO | 00/46231 | 8/2000 |
| WO | WO 00/47598 | 8/2000 |
| WO | 01/96357 | 12/2001 |

OTHER PUBLICATIONS

Banerjee et al., "Protecting Groups That Can Be Removed through Photochemical Electron Transfer: Mechanistic and Product Studies on Photosensitized Release of Carboxylates from Phenacyl Esters", Sep. 5, 1997, The Journal of Organic Chemistry, vol. 62, No. 18, pp. 6245-6251.*

Araki, S. et al.,"Triphenylsulfonium Salt Photochemistry. New evidence for triplet excited state reactions," J. Org. Chem. 53(8):1833-1835 (1988).

Breecher, J., et al.,"Chemically amplified photolithography for the fabrication of high density oligonucleotide arrays," Polymeric Materials Science and Engineering 76:597-598 (1997).

Cameron, J. et al.,Photogeneration of organic bases from o-nitrobenzyl-derived carbamates, J. Amer. Chem. Soc.113:4303-4313 (1991).

de Saizieu, A., et al.,"Bacterial transcript imaging by hybridization of total RNA to oligonucleotide arrays," Nature Biotechnology 16:45-48 (1998).

De Voe, R. et al.,"Photochemistry and photophysics of 'onium salts'," Advances in Photochemistry, 17:313-355 (1992).

Dektar, J. and Hacker, N., "Modulation of π-facial selectivity on diels-alder cycloaddition to isodicyclopentafulvenes by remote para substitutation of an exocyclic phenyl group," J. Org. Chem. 53:1835-1837 (1988).

Drmanac, S., et al.,"Accurate Sequencing by hybridization for DNA diagnostics and individual genomics," Nature Biotechnology 16:54-58 (1998).

Fodor, S. et al.,"Light-directed, Spatially addressable paralle chemical synthesis," Science 251:767-773 (1991).

Fechet, M.J. et al.,"The photogeneration of acid and base within polymer coatings: approaches to polymer curing imaging," Pure & Appl. Chem. 64(9):1239-1248 (1992).

Gao, X., et al.,"Oligonucleotide synthesis using solution photogenerated acids," J. Amer. Chem. Soc. 120:12698-12699 (1998).

Hornbeck, L., et al.,"Digital light processing™ for high-brightness, High-resolution applications," Texas Instruments Digital Video Operations, Feb. 10-12, pp. 1-14 (1997).

Lockhart, D. et al.,"Expression monitoring by hybridization to high-density oligonucleotide arrays", Nature Biotechnology 14:1675-1680 (1996).

Marshall, A. et al., "DNA chips: An array of possibilities," Nature Biotechnology 16:27-31 (1998).

McBride et al.,"An investigation of several deoxynucleoside phosphoramidites useful for synthesizing deoxyoligonucleotides," Tetrahedron Letters 24(3):245-248 (1983).

McGall, G. et al.,"Light-directed synthesis of high-density oligonucleotide arrays using semiconductors photoresists," PNAS, USA 93:13555-13560 (1996).

McGall, G. et al.,"The efficiency of light-directed synthesis of DNA arrays on glass substrates," American Chemical Society 119(22):5081-5090 (1997).

Merrifield, B. et al.,"Solid phase peptide synthesis," Science 232:341-347 (1986).

Patchornik, A. et al.,"Photosensitive Protecting Groups," J. Amer. Chem. Soc. 92:6333-6335 (1970).

Pease A., et al.,"Light-generated oligonucleotide arrays for rapid DNA sequence analysis," PNAS, USA 91:5022-5026 (1994).

Pirrung, M. and Bradley, J.,"Comparison of methods for photochemical phosphoramidite-based DNA synthesis," J. Org. Chem. 60:6270-6276 (1995).

Ramsay, G. et al.,"DNA chips: State-of-the-art," Nature Biotechnology 16:40-44 (1998).

Schena, M., et al.,"Quantitative monitoring of gene expression patterns with a complementary DNA microarray," Science 270:467-470 (1995).

Simpson, P., et al.,"High-throughput genetic analysis using microfabricated 96-sample capillary array electrophoresis microplates," *PNAS, USA* 95:2256-2261 (1998).

Srinvasan, U., et al.,"Self-assembled fluorocarbon films for enhanced stiction reduction," *Transducers '97*, International Conference on Solid-State sensors and Actuators, Jun. 16-19:1399-1402 (1997).

Stewart, J., et al.,"Solid phase peptide synthesis," Pierce Chemical Company, Second edition, pp. 80 (1984).

Sus, V.,"Uber die natur der belichtungsprodukte von diazoverbindungen. Ubergange von aromatischen 6-ringen in 5-ringe", *Liebigs Ann Chem* 556:65-84 (1944), No Translation.

Wallraff, G., et al.,"DNA sequencing on a chip," *Chemtech* 27(2):22-32 (1997).

Weiler, J. et al.,"Hybridisation based DNA screening on peptide nucleic acid (PNA) oligomer arrays," *Nucleic Acids Research* 25(14):2792-2799 (1997).

Welsh, K. et al.,"Photo-CIDNP and nanosecond laser flash photolysis studies on the photodecomposition of triarylsulfonium salts," *J. Org. Chem.* 57(15):4179-4184 (1992).

Wong, C., et al.,"Assembly oligosaccharide libraries with a designed building block and an efficient orthogonal protection-deprotection strategy," *J. Am. Chem. Soc.* 120(8):7137-7138 (1998).

Zheng, M., et al.,"Genetically unstable CXG repeats are structurally dynamic and have a high propensity for folding. An NMR and UV spectroscopic study," *J. Mol. Biol.* 264:323-336 (1996).

Chrisey et al., "Fabrication of Patterned DNA Surfaces," *Nucleic Acids Res.* 24(15):3040-3047 (1996).

Davidson, "A Microlans Direct-Write Concept for Lithography," *SPIE* 3048:346-355 (1997).

Editorial, "To Affinity . . . and Beyond!," *Nature Genetics* 14(4):367-370 (1996).

Feldman and Pevzner, "Gray Code Masks for Sequencing by Hybridization," *Genomics* 23:233-235 (1993.

Fink and Christiansen, *Electronic Engineers Handbook*, 3.sup.rd ed., McGraw Hill, pp. 11-96 and 11-99 (1989).

Forman et al., "Thermodynamics of Duplex Formation and Mismatch Discrimination on Photolithographically Synthesized Oligonucleotide Arrays," Molecular Modeling of Nucleic Acids, American Chemical Society Symposium Series, 206-228 (Apr. 13-17, 1997).

Garner, "Automating the Genome Center," *IEEE Engineering in Medicine and Biology*, pp. 281-283 (1994).

Goodall et al., "Excimer Laser Photolithography with 1:1 Wynne-Dyson Optics," SPIE vol. 922, *Optical/Laser Microlithography* (1988).

Groves et al., "Micropatterning Fluid Lipid Bilayers on Solid-Supports," *Science* 275(5300):651-653 (1997).

Kerth et al., "Excimer Laser Projection Lithography on a Full-Field Scanning Projection System," *IEEE Electron Device Letters, EDL-* 7(5):299-301 (1986).

Kim et al., "Polymer Microstructures Formed by Moulding in Capillaries," *Nature* 376:581-584 (1995).

Kuck et al., "New system for Fast submicron laser direct writing," *SPIE* 2240:506-514 (1995).

McGall et al.,"The Efficiency of Light-Directed Synthesis of DNA Arrays on Glass Substrates," American Chemical Society 119:22, 5081-5090 (1997).

Neff et al., "Two-Dimensional Spatial Light Modulators: A Tutorial," *Proceedings of the IEEE* 78(5):826-855 (1990).

O'Brien et al., Astral, a Hyperspectral Imaging DNA Sequencer, Review of Scientific Instruments 69(5):2141-2146 (1998).

Offner, "New Concepts in Projection Mask Aligners," *Optical Engineering* 14:130-132 (1975).

Park et al., "Block Coploymer Lithography:Periodic Arrays of 1011 Holes in 1 Square Centimeter," *Science* 276:1401-1404 (1997).

Paufler et al., "High-throughput optical direct write lithography," Solid State Technology pp. 175-182 (1997).

Ruff et al., "Broadband Deep-UV High NA Photolithography System," *Optical/Laser Microlithography II, SPIE* 1088:441-446 (1989).

Seltmann et al., "New System for Fast Submicron Optical Direct Writing," *Microelectronic Engineering* 30:123-127 (1996).

Singh-Gasson et al., "Maskless fabrication of light-directed oligonucleotide microarrays using a digital Micromirror array," *Nature Biotechnology* 17:974-978 (1999).

Strachan et al., "A New Dimension for the Human Genome Project: Towards Comprehensive Expression Maps," *Nature Genetics* 16:126-132 (1997).

Sundberg et al., "Spatially-Addressable Immobilization of Macromolecules on Solid Supports," *J Am Chem Soc* 117:12050-12057 (1995).

Yoder, "The State of the Art in Projection Display: An Introduction to the Digital Light Processing (DLP) Technololgy," Texas Instruments, taken from (www.dlp.com/dlp-technology/images/dynamic/dynamic/white_papers/119_Intro_Digital_Light_Processing.pdf).

Opposition Doc. No. 1(febit AG), Jun. 21, 2004.

Opposition Doc. No. 2(Nimble Gen Sys., Inc.) Jun. 21, 2004.

Beaucage S L., et al., "Advances in the Synthesis of Oligonucleotides by the Phosphoramidite Approach," Tetrahedron, Elsevier Science Publishers, Amsterdam, NL, vol. 48, No. 12, 1992, pp. 2223-2311.

Beaucage and Iyler, "The Functionalization of oligonucleotides Via Phosphoramidite Derivatives," Tetradedron 49) 19):1925-1963 (1993).

Bigley and Payling, "Reaction of Organoboranes with Neutral Hydrogen Peroxide," J. Am. Chem. Soc. (B) 1811-1818 (1970).

Chen, et al., "Shape-selective separation of polycyclic aromatic hydrocarbons on protoporphyrin-silica phases . . . ," J. Chromatography A 859: 121-132 (1999).

Crea and Horn, "Synthesis of Oligonucleotides on Cellulose by a Phosphotriester Method," Nucleic Acids Research 8(10):2331-2348 (1980).

Day, et al., "Immobilization of polynucleotides on magnetic particles: Factors influencing hybridization efficiency," Biochem. J. 1991, 278, pp. 735-740.

De Bear, et al., "A Universal Glass Support for Oligonucleotides Synthesis," Nucleosides & Nucleotides 6(5):821-830 (1987).

Dorman, M.A., et al., "Synthesis of oligodeoxynucleotides and oligodeoxynucleotide analogs using phosphoramidite intermediates," Tetrahedron, vol. 40, No. 1, 1984, pp. 95-102.

Doty, et al., "Strand Separation and Specific Recombination in Deoxyribonucleic Acids:Physical Chemical Studies," Proc. Natl. Acad. Sci., USA 46:461-477 (1960).

Dugas and Penney, Bioorganic Chemistry: A Chemical Approach to Enzyme Action, pp. 54-92 (1981).

Ellman et al., "Combinatorial Thinking in Chemistry and Biology," Proc. Natl. Acad. Sci. USA 94:2779-2782 (1997).

Fodor, et al., (1997) American Chemical Society, "The Efficiency of Light-Directed Synthesis of DNA Arrays on Glass Substrates," vol. 119, No. 22, pp. 5081-5090.

Frechet, Jean M.J., "The photogeneration of acid and base within polymer coatings: Approaches to polymer curing and imaging," Pure and Applied Chemistry, vol. 64, No. 9, (1992), pp. 1239-1248.

Fromageot et a., "The Synthesis of Oligoribonucleotides-III. Monocylation o Ribonucleosides and Derivates Via Orthoester Exchange," Tetradedron 23:2315-2331 (1967).

Fryxell et al., "Nucleophilic Displacements in Mixed Self-Assembled Monolayers," Langmuir 12:5064-5275 (1996).

Gao, et al., "A flexible light-directed DNA chip synthesis gated by deprotection using solution photogenerated acids," Nucleic Acids Res. 29:4744-4750 (2001).

Gallop, et al., "Perspective. Application of Combinatorial Technologies to Drug Discovery. 1. Background and Peptide Combinatorial Libraries," J. Med. Chem. 37:1233-1251 (1994).

Gordon et al., "Perspective. Applications of Combinatorial Technologies to Drug Discovery. 2. Combinatorial Organic Synthesis, Library Screening Strategies, and Future Directions," J. Med. Chem. 37:1385-1401 (1994).

Heise et al., "Grafting of Polypeptides on Solid Substrates by Initiation of N-Carboxyanhydride Polymerization of Amino-Terminated Self-Assembled Monolayers," Langmuir 13:723-728 (1997).

Kowollik et al., "5'-O-methylthymidine," Angew. Che. Interbat. Edit. 5:735-736 (1966).

Lebl, M., "Perspective. Parallel Personal Comments on 'Classical' Papers in Combinatorial Chemistry," J. Comb. Chem. 1:3-24 (1999).

Madou, (1997) CRC Press, New York, "Fundamentals of Microfabrication," Preface and Table of Contents.

Marmur and Lane, "Strand Separation and Specific Recombination in Deoxyribonucleic Acids: Biological Studies," Proc. Nat. Acad. Sci., USA 46:453-461 (1960).

Merrifield, R.B., "Solid Phase Peptide Synthesis. 1. The Synthesis of a Tetrapeptide," J. Am. Chem. Soc. 85:2149 (1962).

Monk, David W., "Digital Micromirror Device for Projection Display," Microelectronic Engineering 27 (1995) 489-493.

Netzer et al., "A New Approach to Construction of Artifical monolayer Assemblies," J. Am. Chem. Soc. 105:674-676 (1983).

Netzer et al., "Adsorbed monolayers versus Langmuir-Blodgett monoloayers-why and how? 1. From monolayers to multilayer, by adsorption," J. Thin Solid Films 99:pp. 235-241 (1983).

Netzer et al., "Absorbed monolayers vers Langmuir-Blodgett monolayers-why and how? II. Characterization of built-up films constructed by stepwise adsorption of individual monolayers," J. Thin Solid Films 100:67-76 (1983).

Schwartz et al., "A Universal Adapter for Chemical Synthesis of DNA or RNA on Any Single type of Solis Support," Tetrahedron Letters 36(1):27-30(1995).

Sekine et al., "Facile synthesis of 3'-O-methylthymidine and 3'-dexothymidine and related deoxygenate thymidine derivative: A new method for selective deoxygenation of secondary hydroxyl groups," J. org. Chem. 55:924-928 (1990).

Spitzer et al., "Inhibition of deoxyribonucleases by phosphorothioate groups in oligodeoxyribonucleotides," Nucleic Acids Res. 16:11691-11704 (1988).

Stewart and Young, Solid Phase Peptide Synthesis, pp. 24-66 (1969).

Strobel et al., "Defining the chemical groups essential for Tetrahymena group 1 intron function by nucleotide analog interference mapping," Proc. Natl. Acad. Sci. USA 94:2903-2908 (1997).

Sus, V., (1944) Liebigs Ann Chem., "Uber die Natur de Belichtungsprodukte von Diazoverbindungen. Ubergange von aromatischen 6-Ringen in 5-Ringe," vol. 556, pp. 65-84.

Thompson, et al., (1994) American Chemical Society, "Introduction to Microlithogrpahy," Second Edition, Abstract.

Timofeev et al., "Regioselective immobilization of short oligonucleotides to acrylic copolymer gels," Nucleic Acids Research. 1996, vol. 24, No. 16, pp. 3142-3148.

Usman, N., et al., "Automated Chemical Synthesis of Long Oligoribunocleotides Using 2'-0-Silylated . . . ," Journal of American Chemical Society, vol. 109, No. 25, Dec. 9, 1987 pp. 7845-7854.

Wasserman et al., "Structure and reactivity of alkylsiloxane monolayers formed by reaction of alkytrichlorosilanes on silicon substrates," Langmuir 5:1074-1087 (1989).

* cited by examiner

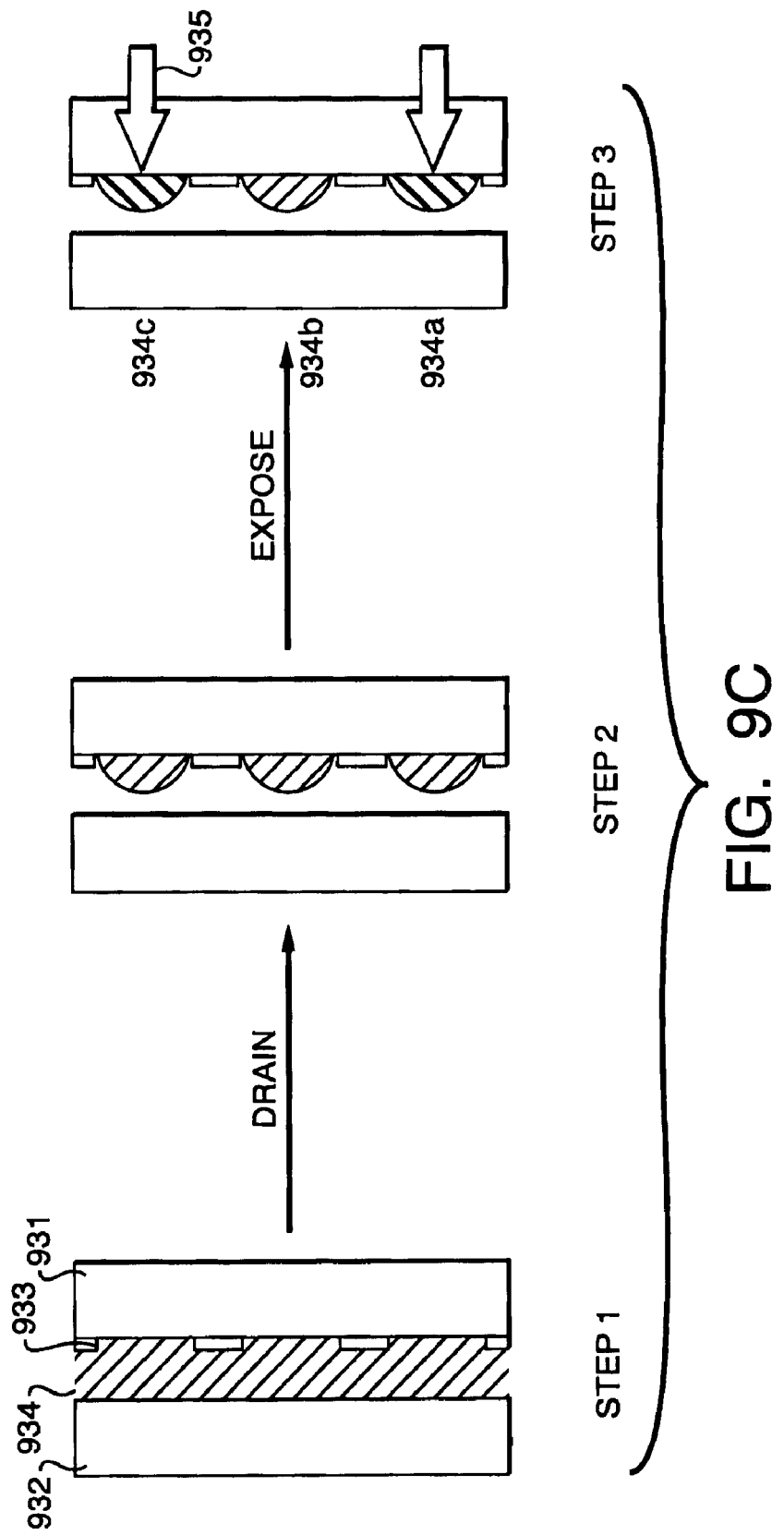

DEVICE FOR CHEMICAL AND BIOCHEMICAL REACTIONS USING PHOTO-GENERATED REAGENTS

This is a Continuation of copending application(s) Ser. No. 10/241,411 filed on Sep. 11, 2002 which is a Continuation of copending application Ser. No. 10/157,442 filed on May 29, 2002 which is a Continuation of patented application Ser. No. 09/248,093 (U.S. Pat. No. 6,426,184) filed on Feb. 10, 1999 which is a conversion of provisional application 60/074,368 filed on Feb. 11, 1998 which is now abandoned.

This application claims the benefit of U.S. Provisional Application No. 60/074,368, filed on Feb. 11, 1998.

BACKGROUND OF THE INVENTION

1. Field of the Invention

The present invention relates to the field of chemical and biochemical reactions. More specifically, the present invention relates to parallel synthesis and assay of a plurality of organic and bio-organic molecules on a substrate surface in accordance with a predetermined spatial distribution pattern. Methods and apparatus of the present invention are useful for preparing and assaying very-large-scale arrays of DNA and RNA oligonucleotides, peptides, oligosacchrides, phospholipids and other biopolymers and biological samples on a substrate surface.

2. Description of the Related Art

Development of modern medicine, agriculture, and materials imposes enormous demands on technological and methodological progress to accelerate sample screening in chemical and biological analysis. Development of parallel processes on a micro-scale is critical to the progress. Many advances have been made in this area using parallel synthesis, robotic spotting, inkjet printing, and microfluidics (Marshall et al., Nature Biotech. 16, 27-31 (1998)). Continued efforts are sought for more reliable, flexible, faster, and inexpensive technologies.

For high-throughput screening applications, a promising approach is the use of molecular microarray (MMA) chips, specifically biochips containing high-density arrays of biopolymers immobilized on solid surfaces. These biochips are becoming powerful tools for exploring molecular genetic and sequence information (Marshall et al., Nature Biotech. 16, 27-31 (1998) and Ramsay, Nature Biotech. 16, 40-44 (1998)). Target molecules have been hybridized to DNA oligonucleotides and cDNA probes on biochips for determining nucleotide sequences, probing multiplex interactions of nucleic acids, identifying gene mutations, monitoring gene expression, and detecting pathogens. Schena, et al., Science 270, 467-460 (1995); Lockhart et al., Nature Biotech. 14, 1675-1680; Weiler, Nucleic Acids Res. 25, 2792-2799 (1997); de Saizieu et al., Nature Biotech. 16, 45-48; Drmanc et al., Nature Biotech. 16, 54-58. The continued development of biochip technology will have a significant impact on the fields of biology, medicine, and clinical diagnosis.

Prior art biochip-fabrication includes direct on-chip synthesis (making several sequences at a time) using inkjets, direct on-chip parallel synthesis (making the whole array of sequences simultaneously) using photolithography, and immobilization of a library of pre-synthesized molecules using robotic spotting (Ramsay, Nature Biotech. 16, 40-44 (1998)). Light-directed on-chip parallel synthesis has been used in the fabrication of very-large-scale oligonucleotide arrays with up to one million sequences on a single elip.

Two major methods have been disclosed: synthesis using photolabile-group protected monomers (Pirrung et al., U.S. Pat. No. 5,143,854 (1992); Fodor et al., U.S. Pat. No. 5,424,186 (1995)) and synthesis using chemical amplification chemistry (Beecher et al., PCT Publication No. WO 98/20967 (1997)). Both methods involve repetitive steps of deprotection, monomer coupling, oxidation, and capping. Photomasks are used to achieve selective light exposure in predetermined areas of a solid substrate surface, on which oligonucleotide arrays are synthesized.

For the synthesis process involving photolabile-protecting groups, the photolabile-protecting groups are cleaved from growing oligonucleotide molecules in illuminated surface areas while in non-illuminated surface areas the protecting groups on oligonucleotide molecules are not affected. The substrate surface is subsequently contacted with a solution containing monomers having a unprotected first reactive center and a second reactive center protected by a photolabile-protecting group. In the illuminated surface areas, monomers couple via the unprotected first reactive center with the deprotected oligonucleotide molecules. However, in the non-illuminated surface areas oligonucleotides remain protected with the photolabile-protecting groups and, therefore, no coupling reaction takes place. The resulting oligonucleotide molecules after the coupling are protected by photolabile protecting groups on the second reactive center of the monomer. Therefore, one can continue the above photo-activated chain propagation reaction until all desired oligonucleotides are synthesized.

For the synthesis process involving chemical amplification chemistry, a planer substrate surface is linked with oligonucleotide molecules (through appropriate linkers) and is coated with a thin (a few micrometers) polymer or photoresist layer on top of the oligonucleotide molecules. The free end of each oligonucleotide molecule is protected with an acid labile group. The polymer/photoresist layer contains a photo-acid precursor and an ester (an enhancer), which, in the presence of $H^+$, dissociates and forms an acid. During a synthesis process, acids are produced in illuminated surface areas within the polymer/photoresist layer and acid-labile protecting groups on the ends of the oligonucleotide molecules are cleaved. The polymer/photoresist layer is then stripped using a solvent or a stripping solution to expose the oligonucleotide molecules below. The substrate surface is then contacted with a solution containing monomers having a reactive center protected by an acid-labile protecting group. The monomers couple via the unprotected first reactive center only with the deprotected oligonucleotide molecules in the illuminated areas. In the non-illuminated areas, oligonucleotide molecules still have their protection groups on and, therefore, do not participate in coupling reaction. The substrate is then coated with a photo-acid-precursor containing polymer/photoresist again. The illumination, deprotection, coupling, and polymer/photoresist coating steps are repeated until desired oligonucleotides are obtained.

There are significant drawbacks in the method involving photolabile-protecting groups: (a) the chemistry used is non-conventional and the entire process is extremely complicated; and (b) the technique suffer from low sequence fidelity due to chemistry complications.

The method of using chemical amplification chemistry has its limitations as well: (a) The method requires application of a polymer/photoresist layer and is not suitable for reactions performed in solutions routinely used in chemical and biochemical reactions since there is no measure provided for separating sites of reaction on a solid surface. (b) In certain circumstances, destructive chemical conditions required for pre- and post-heating and stripping the polymer/photoresist layer cause the decomposition of oligonucleotides on solid surfaces. (c) The entire process is labor intensive and difficult to automate due to the requirement for many cycles (up to 80 cycles if 20-mers are synthesized!) of photoresist coating, heating, alignment, light exposure and stripping. (d) The method is not applicable to a broad range of biochemical reactions or biological samples to which a photo-generated reagent is applied since embedding of biological samples in a polymer/photoresist layer may be prohibitive.

Additional limitations are linked to the use of photomasks in the above two methods: (a) Setup for making a new chip is very expensive due to a large number of photomasks that have to be made. (b) Photolithography equipment is expensive and, therefore, can not be accessed by many interested users. (c) Photolithography processes have to be conducted in an expensive cleanroom facility and require trained technical personnel. (d) The entire process is complicated and difficult to automate. These limitations undermine the applications of oligonucleotide chips and the development of the various MMA-chips.

Therefore, there is a genuine need for the development of chemical methods and synthesis apparatus that are simple, versatile, cost-effective, easy to operate, and that can afford molecular arrays of improved purity.

SUMMARY OF THE INVENTION

The present invention provides methods and apparatus for performing chemical and biochemical reactions in solution using in situ generated photo-products as reagents or co-reagents. These reactions are controlled by irradiation, such as with UV or visible light. Unless otherwise indicated, all reactions described herein occur in solutions of at least one common solvent or a mixture of more than one solvent. The solvent can be any conventional solvent traditionally employed in the chemical reaction, including but not limited to such solvents as $CH_2Cl_2$, $CH_3CN$, toluene, hexane, $CH_3OH$, $H_2O$, and/or an aqueous solution containing at least one added solute, such as NaCl, $MgCl_2$, phosphate salts, etc. The solution is contained within defined areas on a solid surface containing an array of reaction sites. Upon applying a solution containing at least one photo-generated reagent (PGR) precursor (compounds that form at least one intermediate or product upon irradiation) on the solid surface, followed by projecting a light pattern through a digital display projector onto the solid surface, PGR forms at illuminated sites; no reaction occurs at dark (i.e., non-illuminated) sites. PGR modifies reaction conditions and may undergo further reactions in its confined area as desired. Therefore, in the presence of at least one photo-generated reagent (PGR), at least one step of a multi-step reaction at a specific site on the solid surface may be controlled by radiation, such as light, irradiation. Hence, the present invention has great potential in the applications of parallel reactions, wherein at each step of the reaction only selected sites in a matrix or array of sites are allowed to react.

The present invention also provides an apparatus for performing the light controlled reactions described above. One of the applications of the instrument is to control reactions on a solid surface containing a plurality of isolated reaction sites, such as wells (the reactor). Light patterns for effecting the reactions are generated using a computer and a digital optical projector (the optical module). Patterned light is projected onto specific sites on the reactor, where light controlled reactions occur.

One of the applications of the present invention provides in situ generation of chemical/biochemical reagents that are used in the subsequent chemical and biochemical reactions in certain selected sites among the many possible sites present. One aspect of the invention is to change solution pH by photo-generation of acids or bases in a controlled fashion. The pH conditions of selected samples can be controlled by the amount of photo-generated acids or bases present. The changes in pH conditions effect chemical or biochemical reactions, such as by activating enzymes and inducing couplings and cross-linking through covalent or non-covalent bond formation between ligand molecules and their corresponding receptors.

In other aspects of the present invention, photo-generated reagents themselves act as binding molecules that can interact with other molecules in solution. The concentration of the binding molecules is determined by the dose of light irradiation and, thus, the ligand binding affinity and specificity in more than one system can be examined in parallel. Therefore, the method and apparatus of the present invention permits investigating and/or monitoring multiple processes simultaneously and high-throughput screening of chemical, biochemical, and biological samples.

Another important aspect of the present invention is parallel synthesis of biopolymers, such as oligonucleotides and peptides, wherein the method and instrument of the present invention are used for selective deprotection or coupling reactions. These reactions permit controlled fabrication of diverse biopolymers on solid surfaces. These molecular microarray chips (MMA-chips) are used in a wide range of fields, such as functional genomics, diagnosis, therapeutics and genetic agriculture and for detecting and analyzing gene sequences and their interactions with other molecules, such as antibiotics, antitumor agents, oligosaccharides, and proteins. These and other aspects demonstrate features and advantages of the present invention. Further details are made cleat by reference to the remaining portions of the specification and the attached drawings.

The method of the present invention represents fundamental improvements compared to the method of prior arts for parallel synthesis of DNA oligonucleotide arrays (Pirrung et al., U.S. Pat. No. 5,143,854 (1992); Fodor et al., U.S. Pat. No. 5,424,186 (1995); Beecher et al., PCT Publication No. WO 98/20967 (1997)). The present invention advantageously employs existing chemistry, replacing at least one of the reagents in a reaction with a photo-reagent precursor. Therefore, unlike methods of the prior art, which require monomers containing photolabile protecting groups or a polymeric coating layer as the reaction medium, the present method uses monomers of conventional chemistry and requires minimal variation of the conventional synthetic chemistry and protocols.

The improvements made possible by the present invention have significant consequences: (a) The synthesis of sequence arrays using the method of the present invention can be easily integrated into an automated DNA/RNA synthesizer, so that the process of the present invention is much simpler and costs much less. (b) Conventional chemistry adopted by the present invention routinely achieves better than 98% yield per step synthesis of oligonucleotides, which is far better than the 85-95% yield obtained by the previous method of using photolabile protecting groups. Pirrung et al., J. Org. Chem. 60, 6270-6276, (1995); McGall et al., J. Am. Chem. Soc. 119, 5081-5090 (1997); McGall et al., Proc. Natl. Acad. Sci. USA 93, 13555-13560 (1996). The improved stepwise yield is critical for synthesizing high-quality oligonucleotide arrays for diagnostic and clinical applications. (c) Yield of photo-generated products (PGR) is not a major concern in the method of the present invention in contrast to that of the prior art method on incomplete deprotection on photolabile protecting groups. (d) The synthesis process of the present invention can be monitored using conventional chemistry for quality control; this is not possible using the methods of the prior art. (e) The method of the present invention is easily expandable to the synthesis of other types of molecular microarrays, such as oligonucleotides containing modified residues, 3'-oligonucleotides (as opposed to 5'-oligonucleotides obtained in a normal synthesis), peptides, oligosaccharides, combinatory organic molecules, and the like. These undertakings would be an insurmountable task using prior art techniques requiring monomers containing photolabile-protecting groups. The prior art methods require development of new synthetic procedures for each monomer type. In the present invention, modified residues and various monomers that are commercially available can be employed. (f) The present invention can be applied to all types of reactions and is not limited to polymeric reaction media as is the prior art method using chemical amplification reactions. (g) Additionally, the reaction time for each step of synthesis using the conventional oligonucleotide chemistry (5 min. per step) is much shorter than methods using photolabile blocked monomers (>15 min. per step).

Optical patterning in prior art biochip fabrication uses standard photomask-based lithography tools, Karl et al., U.S. Pat. No. 5,593,839 (1997). In general, the number and pattern complexity of the masks increase as the length and variety of oligomers increase. For example, 4×12=48 masks are required to synthesize a subset of dodecanucleotides, and this number may be larger depending on the choice of custom chip. To make a new set of sequences, a new set of masks have to be prepared. More critical is the high precision alignment (on the order of <10 μm resolution) of the successive photomasks, a task that is impossible to achieve without specialized equipment and technical expertise. The technology is only semi-automatic and the method is clearly inflexible and expensive. In addition, the photomask-fabrication process requires expensive cleanroom facilities and demands special technical expertise in microelectronic fields. Therefore, the entire chip-fabrication process is inaccessible to most in the research community.

The present invention replaces the photomasks with a computer-controlled spatial optical modulator so that light patterns for photolithography can be generated by a computer in the same way as it displays black-and-white images on a computer screen. This modification provides maximum flexibility for synthesizing any desirable sequence array and simplifies the fabrication process by eliminating the need for performing mask alignment as in the conventional photolithography, which is time consuming and prone to alignment errors. In addition, both the optical system and the reactor system of the present invention are compact and can be integrated into one desktop enclosure. Such an instrument can be fully controlled by a personal computer so that any bench chemists can make biochips of their own sequence design in a way that is similar to bio-oligomer synthesis using a synthesizer. Moreover, the instrument can be operated in any standard chemical lab without the need for a cleanroom. The present invention can also be easily adopted to streamline production of large quantities of standard biochips or a fixed number of specialized biochips by automated production lines. Obviously, the cost of making biochips can be significantly reduced by the method and apparatus of the present invention and, therefore, the accessibility of the biochip technology to research and biomedical communities can be significantly increased.

Most importantly, the method of the present invention using photo-generated reagents in combination with a computer-controlled spatial optical modulator makes MMA-chip fabrication a routine process, overcoming limitations of the prior art methods.

BRIEF DESCRIPTION OF THE DRAWINGS

FIG. 9C illustrates an isolation mechanism using a patterned non-wetting film on a substrate.

DETAILED DESCRIPTION OF THE INVENTION

Figure 1:
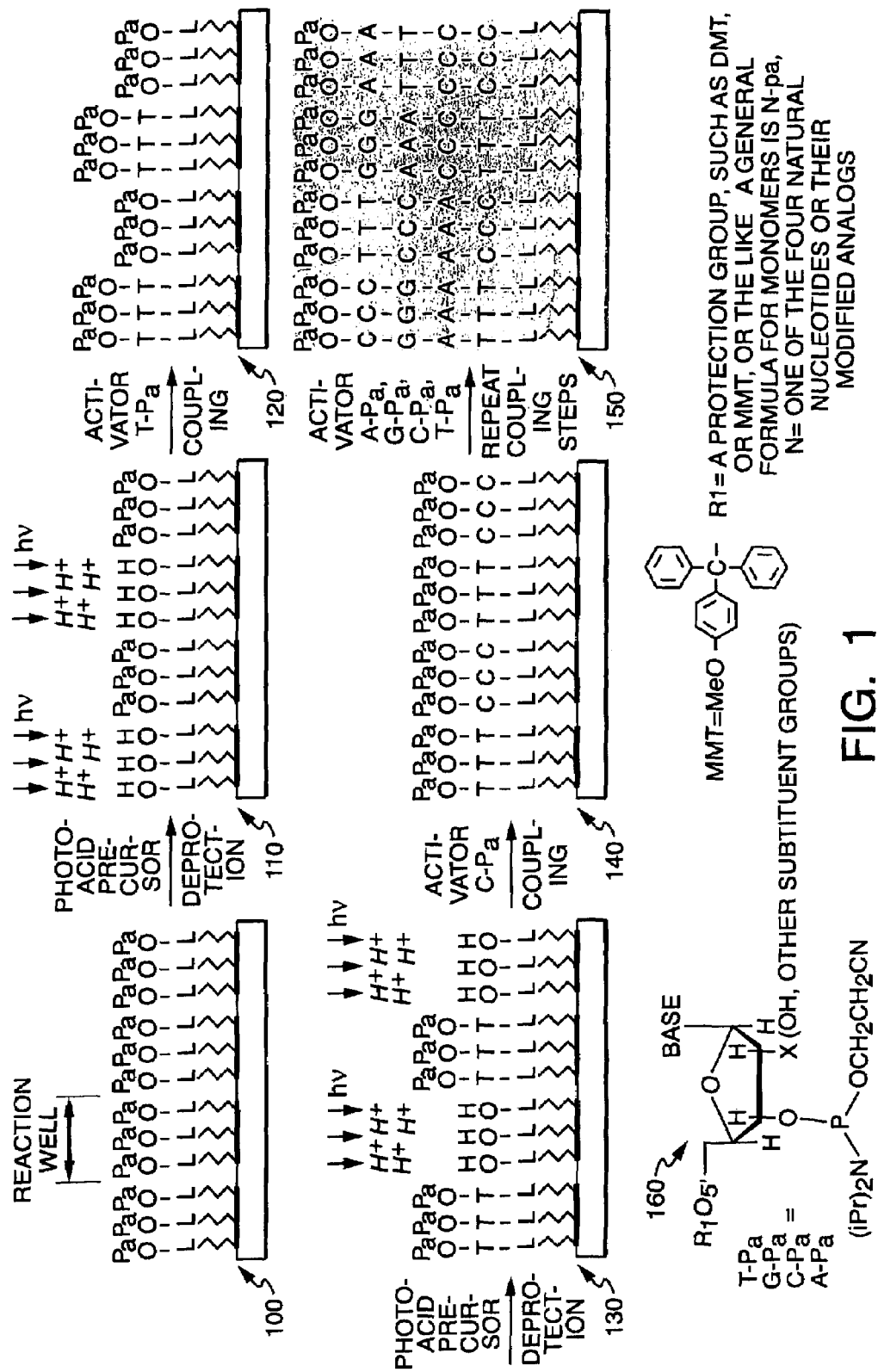
FIG. 1 is a drawing of oligonucleotide synthesis using photo-generated acids. L—linker group; $P_a$—acid-labile protecting group; $H^+$—photo-generated acid; T, A, C, and G—nucleotide phosphoramidite monomers; hv—light exposure.

Method for Chemical/Biochemical Reactions Using Photo-Generated Reagents (PGR)

The present invention provides a method for solution based photochemical reactions involving reagents generated in situ by irradiation. A conventional chemical/biochemical reaction occurs between at least one reactant (generically denoted as "A") and at least one reagent (generically denoted as "R") to give at least one product as depicted below:

A+R→A'+R'

The present invention is to provide reaction conditions that are controlled by irradiation with light. Mainly, the R in the reaction above is photo-generated. The photo-generated reagent (PGR) functions the same as a reagent conventionally used and, thus, the reaction proceeds in an otherwise conventional way. The overall photo-controlled reaction is depicted below.

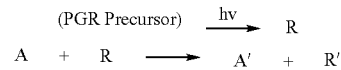

In some embodiments of the present invention, PGR precursors (Table 1) are photo-generated acid precursors that yield $H^+$ in the form of $R_1CO_2H$, $R_1PO_3H$, $R_1SO_3H$, $H^+X^-$ ($R_1$=H, alkyl ($C_1$-$C_{12}$), aryl (aromatic structures containing phenyl), or their substituted derivatives (substitutions=halogen atoms, $NO_2$, CN, OH, $CF_3$, C(O)H, $C(O)CH_3$, $C(O)R_2$, $SO_2CH_3$, $SO_2R_2$, $OCH_3$, $OR_2$, $NH_2$, $NHR_2$, $NR_2R_3$ ($R_2$ and $R_3$=alkyl or aryl ($C_1$-$C_{12}$)); X=halogen atoms, inorganic salt ions) or the like. Photo-generated acids are also complexes, such as $M_mX_n$ (Lewis acids, m and n are number of atoms) formed upon irradiation. In other embodiments of the present invention, PGR precursors (Table 1) are photo-generated base precursors that yield a base, such as an amine, an oxide or the like, upon irradiation.

TABLE 1A

Examples of Photo-Generated Reagent Precursors and Their Products

| Photo-Reagent Precursor | Chemical Structure | Reagent Generated |
|---|---|---|
| diazonium salts | 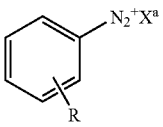<br>X = $B(R_1)_4$, $Al(R_1)_4$<br>($R_1$ = halogen); R = H, halogen,<br>$NO_2$, CN, $SO_2R_5$, OH, $OCH_3$,<br>$SCH_3$, $CF_3$, $OR_5$, $SR_5$,<br>$CH_3$, t-butyl, $C_1$-$C_{12}$- alkyl, aryl<br>and their substituted derivatives$^a$,<br>$NH_2$, $HNR_5$, $N(R_5)_2$,<br>($R_5$ = $C_1$-$C_{12}$-alkyl,<br>aryl and their substituted derivatives$^a$);<br>$COR_6$ ($R_6$ = H, $NH_2$,<br>$HNR_5$, $OR_5$, $C_1$-$C_{12}$-alkyl,<br>aryl and their derivatives). R and $R_{1-6}$<br>each can be the same or different each<br>time they appear in the formula. | $B(R_1)_3$, $Al(R_1)_3$ |
| perhalomethyl triazines | 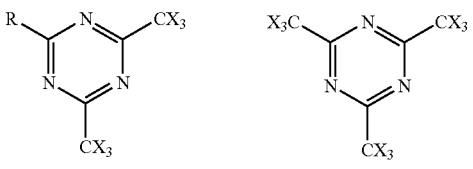<br>X = halogen, R = methyl, phenyl,<br>$C_1$-$C_{12}$-alkyl, aryl and their<br>substituted derivatives. | HX |
| halobisphenyl A | 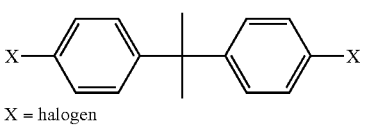<br>X = halogen | HX |

TABLE 1A-continued

Examples of Photo-Generated Reagent Precursors and Their Products

| Photo-Reagent Precursor | Chemical Structure | Reagent Generated |
|---|---|---|
| o-nitrobenzaldehyde | 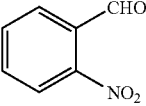<br>R = CH$_3$, CF$_3$, Ph,<br>C$_1$-C$_{12}$-alkyl, aryl<br>and their substituted derivatives. | 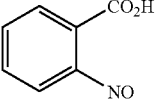 |
| imidylsulfonyl esters | 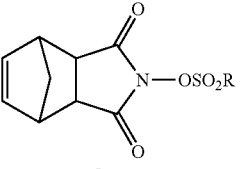<br>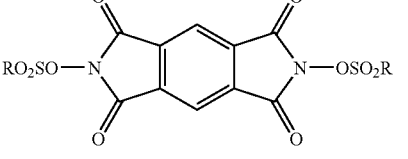<br>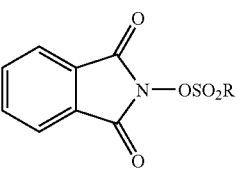<br>R = CH$_3$, CF$_3$, Ph,<br>or C$_1$-C$_{12}$-alkyl, aryl<br>and their substituted derivatives. | RSO$_3$H |
| diaryliodonium salts | 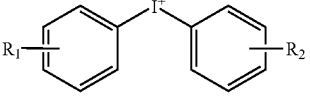<br>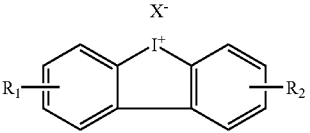<br>X = B(R$_1$)$_4$, Al(R$_1$)$_4$<br>(R$_1$ = halogen); R = H, halogen,<br>NO$_2$, CN, SO$_2$R$_5$, OH, OCH$_3$,<br>SCH$_3$, CF$_3$, OR$_5$, SR$_5$,<br>CH$_3$, t-butyl, C$_1$-C$_{12}$- alkyl,<br>aryl and their substituted derivatives, NH$_2$,<br>HNR$_5$, N(R$_5$)$_2$, (R$_5$ =<br>C$_1$-C$_{12}$-alkyl, aryl and their<br>substituted derivatives); COR$_6$<br>(R$_6$ = H, NH$_2$, HNR$_5$,<br>OR$_5$, C$_1$-C$_{12}$-alkyl, aryl and<br>their derivatives). R and R$_{1-6}$ each can be<br>the same or different each time they appear in the<br>formula. | HX, BF$_3$ |

TABLE 1A-continued

Examples of Photo-Generated Reagent Precursors and Their Products

| Photo-Reagent Precursor | Chemical Structure | Reagent Generated |
|---|---|---|
| sulfonium salts | 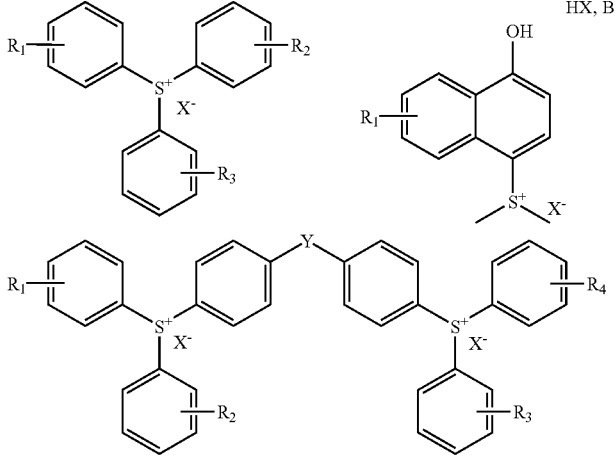 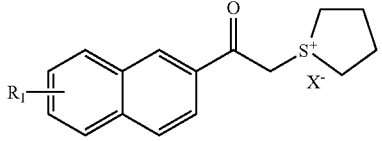  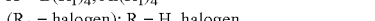<br>X = B(R$_1$)$_4$, Al(R$_1$)$_4$<br>(R$_1$ = halogen); R = H, halogen,<br>NO$_2$, CN, SO$_2$R$_5$, OH, OCH$_3$,<br>SCH$_3$, CF$_3$, OR$_5$, SR$_5$,<br>CH$_3$, t-butyl, C$_1$-C$_{12}$-<br>alkyl, aryl and their substituted derivatives,<br>NH$_2$, HNR$_5$, N(R$_5$)$_2$,<br>(R$_5$ = C$_1$-C$_{12}$-alkyl, aryl and<br>their substituted derivatives); COR$_6$<br>(R$_6$ = H, NH$_2$, HNR$_5$,<br>OR$_5$, C$_1$-C$_{12}$-alkyl, aryl and<br>their derivatives). R and R$_{1-6}$ each can be<br>the same or different each time they appear<br>in the formula. Y = O, S. | HX, BF$_3$ |
| diazosulfonate | 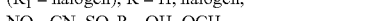 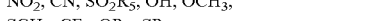<br>R = phenyl, CH$_3$, CF$_3$,<br>C$_1$-C$_{12}$-alkyl, aryl and their<br>substituted derivatives, R$_1$ = H,<br>halogen, NO$_2$, CN, SO$_2$R$_5$, OH,<br>OCH$_3$, SCH$_3$, CF$_3$, OR$_6$,<br>SR$_5$, CH$_3$, t-butyl,<br>C$_1$-C$_{12}$-alkyl, aryl and their<br>substituted derivatives, NH$_2$, HNR$_5$,<br>N(R$_5$)$_2$, (R$_5$ = C$_1$-C$_{12}$-<br>alkyl, aryl and their substituted derivatives); | RSO$_3$H R$_1$PhSO$_3$H |

TABLE 1A-continued

Examples of Photo-Generated Reagent Precursors and Their Products

| Photo-Reagent Precursor | Chemical Structure | Reagent Generated |
|---|---|---|
| | $COR_6$ ($R_6$ = H, $NH_2$, $HNR_5$, $OR_5$, $C_1$-$C_{12}$- alkyl, aryl and their derivatives). R and $R_{1-6}$ each can be the same or different each time they appear in the formula. | |
| diarylsulfones | 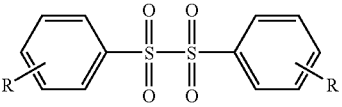<br>R = H, halogen, $NO_2$, CN, $SO_2R_5$, OH, $OCH_3$, $SCH_3$, $CF_3$, $OR_5$, $SR_5$, $CH_3$, t-butyl, $C_1$-$C_{12}$- alkyl, aryl and their substituted derivatives, $NH_2$, $HNR_5$, $N(R_5)_2$, ($R_5$ = $C_1$-$C_{12}$-alkyl, aryl and their substituted derivatives); $COR_6$ ($R_6$ = H, $NH_2$, $HNR_5$, $OR_5$, $C_1$-$C_{12}$- alkyl, aryl and their derivatives). R and $R_{1-6}$ each can be the same or different each time they appear in the formula. | 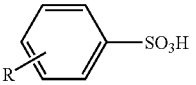 |
| 1,2-diazoketones | 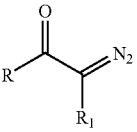<br>R, $R_1$ = H, halogen, $NO_2$, CN, $SO_2R_5$, OH, $OCH_3$, $SCH_3$, $CF_3$, $OR_5$, $SR_5$, $CH_3$, t-butyl, $C_1$-$C_{12}$-alkyl, aryl and their substituted derivatives, $NH_2$, $HNR_5$, $N(R_5)_2$, ($R_5$ = $C_1$-$C_{12}$-alkyl, aryl and their substituted derivatives); $COR_6$ ($R_6$ = H, $NH_2$, $HNR_5$, $OR_5$, $C_1$-$C_{12}$- alkyl, aryl and their derivatives). R and $R_{1-6}$ each can be the same or different each time they appear in the formula. R, $R_1$ can be the same or different, or can be connected through covalent bonds. R, $R_1$ = aryl, alkyl, and their substituted derivatives. | 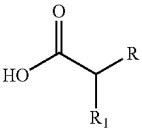 |
| examples of diazoketones: 2-diazo-1-oxo-5-sulfonyl or 2-diazo-1-oxo-4-sulfonyl naphthanol esters | 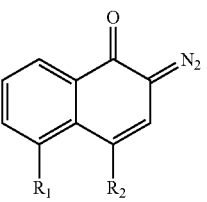<br>$R_1$, $R_2$ = H, $SO_2R$ (R = $C_1$-$C_{12}$-alkyl, aryl, and their substituted derivatives). | 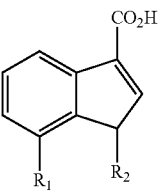 |

TABLE 1A-continued

Examples of Photo-Generated Reagent Precursors and Their Products

| Photo-Reagent Precursor | Chemical Structure | Reagent Generated |
|---|---|---|
| | 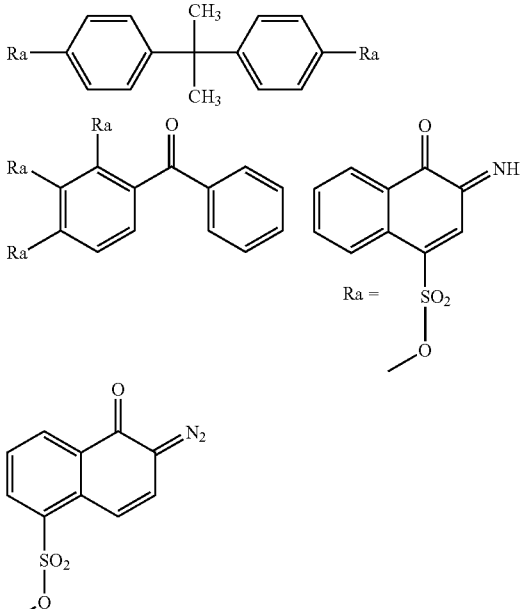 | |
| examples of diazoketones: | 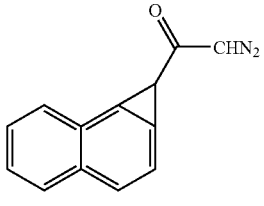 | 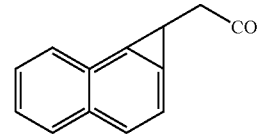 |
| examples of diazoketones: diazo-Meldrums' acid | 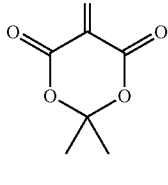 | 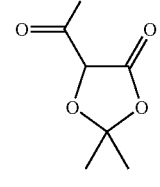 |
| arylazide derivatives | 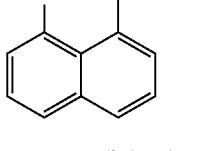<br>R = $C_1$-$C_{12}$-alkyl, aryl, and their substituted derivatives; $R_1$ = H, $C_1$-$C_{12}$-alkyl, aryl, and their substituted derivatives. | $RCO_2H$ or 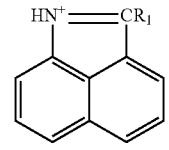 |
| arylazide derivatives | 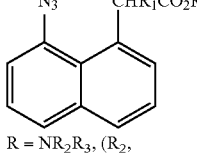<br>R = $NR_2R_3$, ($R_2$, $R_3$ = H, $C_1$-$C_{12}$-alkyl, aryl, and their substituted derivatives), $R_1$ = H, $C_1$-$C_{12}$-alkyl, | $HNR_2R_3$ |

TABLE 1A-continued

Examples of Photo-Generated Reagent Precursors and Their Products

| Photo-Reagent Precursor | Chemical Structure | Reagent Generated |
|---|---|---|
| | aryl, and their substituted derivatives. | |
| benzocarbonates or carbamates | [structure of phenyl ketone with -OC(O)R group and CH$_3$]<br>R = NR$_1$R$_2$ (R$_1$, R$_2$= H, C$_1$-C$_{12}$-alkyl, aryl and their substituted derivatives), C$_1$-C$_{12}$-alkyl, aryl and their substituted derivatives. | RCO$_2$H or HNR$_1$R$_2$ |
| dimethoxybenzoinyl carbonates or carbamates | [structure with R(O)CO, R$_1$CR$_2$, dimethoxybenzene with MeO and OMe]<br>R = NR$_3$R$_4$ (R$_3$, R$_4$ = H, C$_1$-C$_{12}$-alkyl, aryl and their substituted derivatives), C$_1$-C$_{12}$-alkyl, aryl and their substituted derivatives; R$_1$, R$_2$ = H, C$_1$-C$_{12}$-alkyl, COPh, aryl and their substituted derivatives. | RCO$_2$H or HNR$_3$R$_4$ |
| o-nitrobenzyloxycarbo-nates or carbamates | [structure of nitrobenzene with R$_1$, R$_2$, R$_3$, R$_4$, OR substituents]<br>R = COR$_5$ (R$_5$ = CF$_3$, OR$_6$, NH$_2$, HNR$_6$, C$_1$-C$_{12}$-alkyl, aryl and their derivatives (R$_6$ = H, C$_1$-C$_3$-alkyl, aryl and their substituted derivatives)), SO$_2$R$_5$, PO$_2$R$_5$, CONR$_6$R$_7$ (R$_7$ = H, C$_1$-C$_{12}$-alkyl, aryl and their substituted derivatives), R$_1$, R$_2$ = H, halogen, NO$_2$, CN, SO$_2$R$_5$, OH, OCH$_3$, OR$_a$, N(R$_a$)$_2$, (R$_a$ = C$_1$-C$_3$-alkyl, aryl and their substituted derivatives); CH$_2$, t-butyl, C$_1$-C$_{12}$-alkyl, aryl and their substituted derivatives; R$_3$, R$_4$ = H, C$_1$-C$_{12}$-alkyl, aryl, and their substituted derivatives. | R$_5$CO$_2$H<br>R$_5$PO$_3$H<br>R$_5$SO$_3$H<br>CF$_3$SO$_3$H<br>or HNR$_6$R$_7$ |
| nitrobenzenesul-phenyl | [structure of O$_2$N-phenyl-S-OC(O)R with N$_2$O]<br>R = CF$_3$, NR$_1$R$_2$ (R$_1$, R$_2$ = H, C$_1$-C$_3$-alkyl, aryl and their substituted derivatives), C$_1$-C$_{12}$-alkyl, aryl and their derivatives. | RCO$_2$H or HNR$_1$R$_2$ |

TABLE 1A-continued

Examples of Photo-Generated Reagent Precursors and Their Products

| Photo-Reagent Precursor | Chemical Structure | Reagent Generated |
|---|---|---|
| o-nitroanilines | 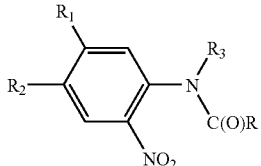<br>$R = CF_3$, $NR_4R_5$<br>($R_4$, $R_5$ = H, $C_1$-$C_{12}$-alkyl,<br>aryl and their substituted derivatives), alkyl,<br>aryl and their derivatives; $R_1$, $R_2$ =<br>H, halogen, $NO_2$, CN, $SO_2R_4$,<br>OH, $OCH_3$, $OR_a$, $N(R_4)_2$;<br>$CH_3$, t-butyl, $C_1$-$C_{12}$-alkyl, aryl<br>and their substituted derivatives;<br>$R_3$ = H, $C_1$-$C_{12}$-alkyl,<br>aryl and their substituted derivatives. | $RCO_2H$ or $HNR_4R_5$ |

TABLE 1B

Examples of Radiation Sensitizers for PGR Reactions[a]

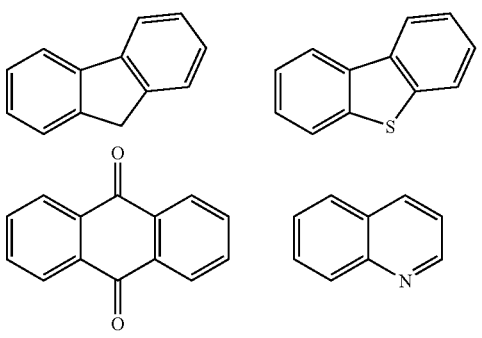

photo-sensitizer: Photosensitizers include but not limited to the following: benzophenone, acetophenone, benzoinyl $C_1$-$C_{12}$-alkyl ethers benzoyl triphenylphosphine oxide, anthracene thioxanthone, chlorothioxanthones, pyrene, $Ru^{2+}$complexes, their various substituted derivatives, and the like.

TABLE 1C

Examples of Stabilizers for PGR Reactions[a]

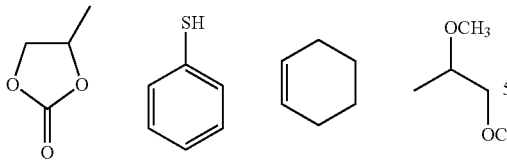

stabilizer: R-H stabilizers include but not limited to the following: propylene carbonate, propylene glycol ethers, t-butane, t-butanol, thiols, cyclohexene, their substituted derivatives and the like.

[a]Substituted derivatives contain at least one of the substituent groups, which include but not limited to halogen, $NO_2$, CN, OH, SH, $CF_3$, C(O)H, C(O)$CH_3$, $C_1$-$C_3$-acyl, $SO_2CH_3$, $C_1$-$C_3$-$SO_2R_2$, $OCH_3$, $SCH_3$, $C_1$-$C_3$- $OR_2$, $C_1$-$C_3$-$SR_2$, $NH_2$, $C_1$-$C_3$-$NHR_2$, $C_1$-$C_3$-$N(R_2)_2$ ($_{R2}$ = alkyl, can be the same or different each time they appear in the formula).

In some embodiments of the present invention, PGR precursors are used in combination with co-reagents, such as radiation sensitizers. One specific example is the use of photosensitizers, which are compounds of lower excitation energies than the PGR used. Irradiation excites photosensitizers, which in turn initiate conversion of PGR precursors to give PGR. The effect of the photosensitizer is to shift the excitation wavelength used in photochemical reactions and to enhance the efficiency of the formation of photo-generated reagents. Accordingly, in one embodiment, the present invention makes use of, but is not limited to, photosensitizers as co-reagents in PGR reactions. Many radiation sensitizers are known to those skilled in the art and include those previously mentioned. It is to be understood that one of ordinary skills in the art will be able to readily identify additional radiation sensitizers based upon the present disclosure.

In preferred embodiments of the present invention, the substrate surface is solid and substantially flat. As non-limiting examples, the substrate can be a type of silicate, such as glass, Pyrex or quartz, a type of polymeric material, such as polypropylene or polyethylene, and the like. The substrate surfaces are fabricated and derivatized for applications of the present invention.

Photo-Generated Acid (PGA) Deprotection and Oligonucleotide Synthesis

According to one embodiment of the present invention (FIGS. 1 and 2), linker molecules are attached to a substrate surface on which oligonucleotide sequence arrays are to be synthesized (the linker is an "initiation moiety", a term also broadly including monomers or oligomers on which another monomer can be added). The methods for synthesis of oligonucleotides are known, McBride et al., Tetrahedron Letter 24, 245-248 (1983). Each linker molecule contains a reactive functional group, such as 5'-OH, protected by an acid-labile protecting group 100. Next, a photo-acid precursor or a photo-acid precursor and its photosensitizer (Table 1) are applied to the substrate. A predetermined light pattern is then projected onto the substrate surface 110. Acids are produced at the illuminated sites, causing cleavage of the acid-labile protecting group (such as DMT) from the 5'-OH, and the terminal OH groups are free to react with incoming monomers (FIG. 2, "monomers" as used hereafter are broadly defined as chemical entities, which, as defined by chemical structures, may be monomers or oligomers or their derivatives). No acid is produced at the dark (i.e. non-illuminated sites) and, therefore, the acid labile protecting groups of the linker molecules remain intact (a method of preventing H⁺ diffusion between adjacent sites will be described later). The substrate surface is then washed and subsequently contacted with the first monomer (e.g., a nucleophosphoramidite, a nucleophosphonate or an analog compound which is capable of chain growing), which adds only to the deprotected linker molecules under conventional coupling reaction conditions 120. A chemical bond is thus formed between the OH groups of the linker molecules and an unprotected reactive site (e.g., phosphorus) of the monomers, for example, a phosphite linkage. After proper washing, oxidation and capping steps, the addition of the first residue is complete.

The attached nucleotide monomer also contains a reactive functional terminal group protected by an acid-labile group. The substrate containing the array of growing sequences is then supplied with a second batch of a photo-acid precursor and exposed to a second predetermined light pattern 130. The selected sequences are deprotected and the substrate is washed and subsequently supplied with the second monomer. Again, the second monomer propagates the nascent oligomer only at the surface sites that have been exposed to light. The second residue added to the growing sequences also contains a reactive functional terminal group protected by an acid-labile group 140. This chain propagation process is repeated until polymers of desired lengths and desired chenucal sequences are formed at all selected surface sites 150. For a chip containing an oligonucleotide array of any designated sequence pattern, the maximum number of reaction steps is 4×n, where n is the chain length and 4 is a constant for natural nucleotides. Arrays containing modified sequences may require more than 4×n steps.

PGA Activated Coupling Reaction and Oligonucleotide Synthesis

Figure 3:
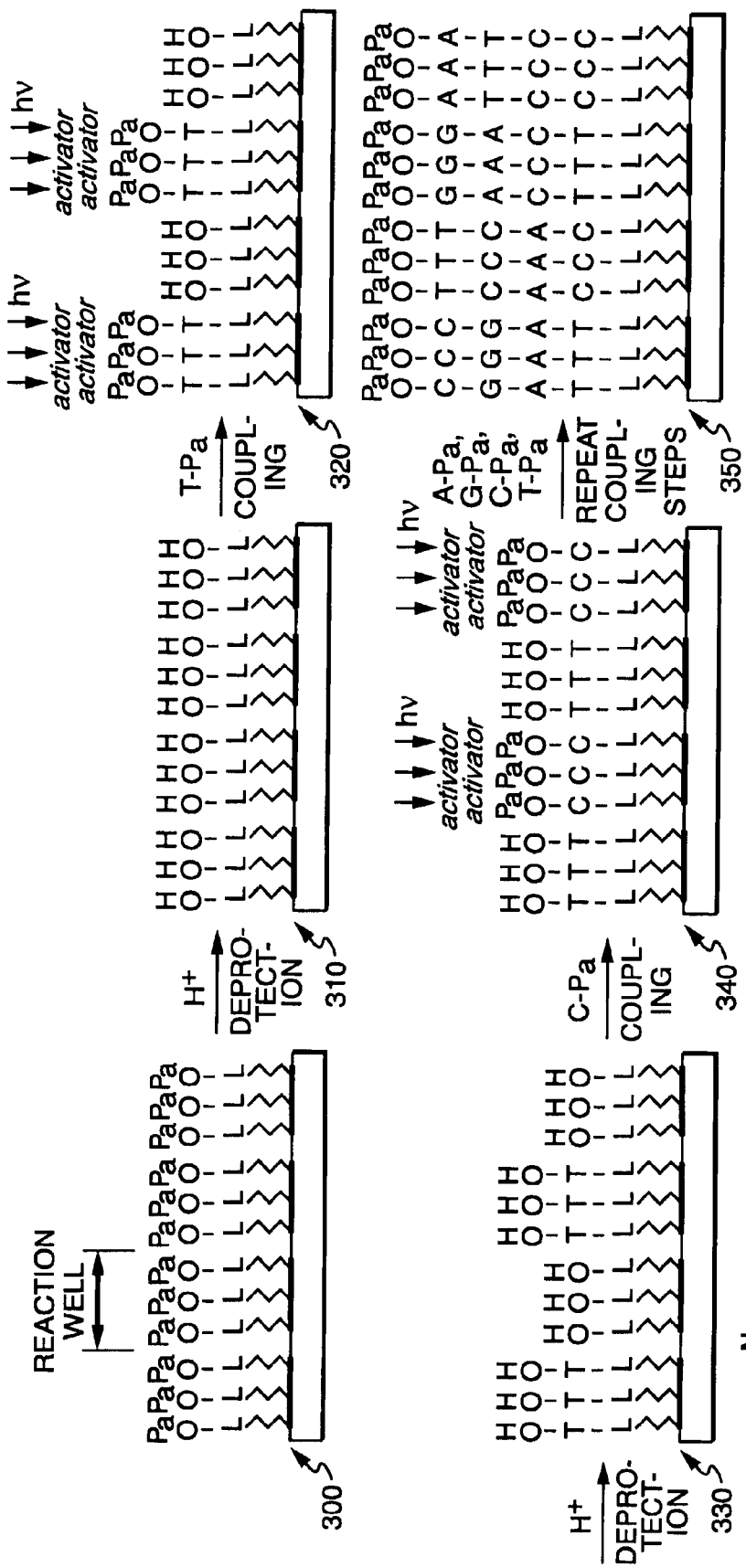
FIG. 3 is a drawing of oligonucleotide synthesis using photo-generated reagents. The process is the same as shown in FIG. 1 except that a photo-generated activator, such as dimethoxybenzoinyltetrazole, is used, while the deprotection step is accomplished using a conventional acid.

According to another embodiment of the present invention (FIG. 3), a photo-activator precursor, such as a compound containing tetrazole linked to a photolabile group, is used. Linker molecules are attached to a substrate surface, on which oligonucleotide sequence arrays are to be synthesized 300. Acid labile protection groups on linkers are deprotected 310. Next, a photo-activator precursor or a photo-activator precursor and its photosensitizer (Table 1) are applied to the substrate. A predetermined light pattern is then projected onto the substrate surface 320. At the illuminated sites, activator molecules are produced and monomers are coupled to the linker. At the non-illuminated sites, no activator molecules are produced and, therefore, no reaction occurs (a method of preventing activator diffusion between adjacent sites will be described later). After proper washing, oxidation and capping steps, the addition of the first residue is complete.

The attached nucleotide monomer also contains a protected functional terminal group. The substrate containing the array of growing sequences is then contacted with a second batch of acid 330. Sequences are deprotected and the substrate is washed and subsequently contacted with the second monomer. Again, the second monomer propagates only at the surface sites that have been exposed to light 340. This chain propagation process is repeated until polymers of desired lengths and chemical sequences are formed at all selected surface sites 350.

Alternative Embodiments of Oligonucleotide Synthesis Using Photo-Generated Reagents In some embodiments of the present invention, the appropriate monomers used in the coupling steps 120, 140, 150, 320, 340 and 350 are nucleotide analogs. The reaction of these monomers proceeds as described in FIGS. 1 and 3 to give oligonucleotides containing modified residues.

In some embodiments of the present invention, the appropriate monomers used in the coupling steps 120, 140, 150, 320, 340 and 350 are those containing an acid labile protecting group, such as DMT, at the 3'-OH position. The reaction of these monomers proceeds as described in FIGS. 1 and 3 but with sequence grown in an opposite orientation compared to that using 5'-OH protected monomers. Such syntheses produce oligonucleotides containing a terminal 3'-OH, which are of particular use as primers for in situ polymerase chain reactions (PCR).

Photo-generated reagents and Photosensitizers

The use of PGR in the present invention permits chemical/biochemical reactions under conventional conditions. The occurrence of the reaction is controlled, however, by in situ formation of at least one reagent upon irradiation. In some embodiments, irradiation is from a light source emitting UV and visible light. Heat, IR and X-ray irradiation are also sources of irradiation. A PGR is produced by irradiation of a PGR precursor or a photosensitizer (which in turn transfers its energy to a PGR precursor). Chemical transformation occurs to yield at least one product (PGR), which is an intermediate or a stable compound. PGR is from part of the PGR precursor molecule dissociated from the parent structure or a rearranged structure of the PGR precursor. PGR may be an acid, a base, a nucleophile, an electrophile, or other reagents of specific reactivities (Table 1).

In some embodiments of the present invention, improved reaction yields and/or suppression of side reactions are achieved by pre-irradiation activation of at least one PGR before mixing with other reactants. Pre-irradiation activation allows time for active reaction intermediates, such as free radical species generated during irradiation, to diminish and for products, such as H⁺, to reach a stable concentration. Improved reaction yields and/or suppression of side reactions are also achieved if at least one suitable stabilizer is used. One example is to provide at least one reagent to reduce the lifetime of active reaction intermediates such as a free radical species generated during irradiation, and to provide a low energy source of hydrogen. This is illustrated by the following reactions of generating H⁺ from sulfonium salts ($Ar_3S^+ X^-$).

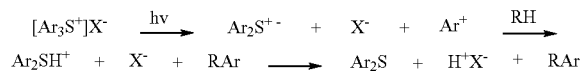

$$[Ar_3S^+]X^- \xrightarrow{h\nu} Ar_2S^{+\cdot} + X^- + Ar^+ \xrightarrow{RH}$$
$$Ar_2SH^+ + X^- + R\text{Ar} \longrightarrow Ar_2S + H^+X^- + R\text{Ar}$$

RH compounds in the above equation are stable and are good H donors. Examples of such compounds include propylenecarbonate (one of the major components of UVI 6974 and UVI 6990), t-butane, cyclohexene, and the like (Table IC).

Photo-acid precursors within the scope of the present invention include any compound that produces PGA upon irradiation. Examples of such compounds include diazoketones, triarylsulfonium, iodonium salts, o-nitrobenzyloxycarbonate compounds, triazine derivatives and the like. Representative examples of these compounds are illustrated in Table 1A. The table is compiled based on data found in following references: Süs et al., *Liebigs Ann. Chem.* 556, 65-84 (1944); Hisashi Sugiyama et al., U.S. Pat. No. 5,158,885 (1997); Cameron et al., J. Am. Chem. Soc. 113, 4303-4313 (1991); Fréchet, *Pure & Appl. Chem.* 64, 1239-1248 (1992); Patchornik et al., J. Am. Chem. Soc. 92, 6333-6335 (1970).

An example of a photo-acid precursor is triarylsulfonium hexafluoroantimonate derivatives (Dektar et al., *J. Org. Chem.* 53, 1835-1837 (1988); Welsh et al., *J. Org. Chem.* 57, 4179-4184 (1992); DeVoe et al., *Advances in Photochemistry* 17, 313-355 (1992)). This compound belongs to a family of onium salts, which undergo photodecompositions, either directly or sensitized, to form free radical species and finally produce diarylsulfides and H$^+$ (see above).

Another example of a photo-acid precursor is diazonaphthoquionesulfonate triester ester, which produces indenecarboxylic acid upon UV irradiation at λ>350 nm. The formation of the acid is due to a Wolff rearrangement through a carbene species to form a ketene intermediate and the subsequent hydration of ketene (Süs et al., *Liebigs Ann. Chem.* 556, 65-84 (1944); Hisashi Sugiyama et al., U.S. Pat. No. 5,158,885 (1997)).

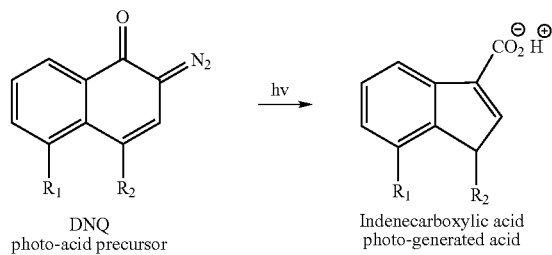

DNQ
photo-acid precursor

Indenecarboxylic acid
photo-generated acid

These photolytic intermediates and products have been extensively used in cationic and radical catalyzed polymerizations for high-resolution microimaging photolithograpy.

Photo-acid precursor compounds have been widely used for many years in printing and microelectronics industries as a component in photoresist formulations (Willson, in "Introduction to microlithography", Thompson et al. Eds., Am. Chem. Soc.: Washington D. C., (1994)). These reactions are, in general, fast (complete in a matter of seconds or minutes), proceed under mild conditions (room temperature, neutral solution), and the solvents used in the photoreactions (haloalkanes, ketones, esters, ethers, toluene, and other protic or aprotic polar solvents) are compatible with oligonucleotide (McBride et al., *Tetrahedron Letter* 24, 245-248 (1983))[6] or other organic solution chemistry. Among the photo-generated acids listed in Table 1, selections are made for chemistry compatibility to minimize side reactions. The chemical properties, such as acidity of the photo-generated acids can be adjusted by different substitution groups on the ring or chain moieties. For instance, the electronegative sulfonate group in the indenecarboxylic acid formed helps to stabilize the negative charge on the carboxylic group attached to the same ring moiety to give an acid that effectively deprotects the 5'-O-DMT group (FIG. 2) in a way comparable to that of using the conventional trichloroacetic acid (TCA). In general, electron-withdrawing groups, such as $O_2SOR$, $NO_2$, halogens, C(=O)R(R=aryl, alkyl, and their substituted derivatives, or $XR_1$ (X=S, O, N; $R_1$=aryl, alkyl, and their substituted derivatives) increase the strength of the corresponding acids. Electron donating groups, such as OR(R=aryl, alkyl, and their substituted derivatives), decrease the strength of the corresponding acids. The availability of acids of different strengths provides a repertoire of reagents for a range of acid-catalyzed deprotection reactions.

Photo-base precursors within the scope of the present invention include any compound that produces PGB upon irradiation. Examples of such compounds include o-benzocarbamates, benzoinylcarbamates, nitrobenzyloxyamine derivatives listed in Table 1, and the like. In general, compounds containing amino groups protected by photolabile groups can release amines in quantitative yields. The photoproducts of these reactions, i.e., in situ generated amine compounds, are, in this invention, the basic reagents useful for further reactions.

Photo-reagent precursors within the scope of the present inversion include any compound that produces a reagent required by a chemical/biochemical reaction upon irradiation. Examples of such compounds include 1-(dimethoxylbenzoinyl)tetrazole (heterocyclic compound tetrazole is a PGR), dimethoxylbenzoinylOR$_1$ (R$_1$OH is a PGR, R$_1$=alkyl, aryl and their substituted derivatives), sulfonium salts (thiol ether Ar$_2$S is a PGR), and the like.

Photosensitizers within the scope of the present invention include any compound that are sensitive to irradiation and able to improve excitation profile of PGR by shifting its excitation wavelength and enhancing efficiency of irradiation. Examples of such compounds include benzophenone, anthracene, thioxanthone, their derivatives (Table 1B), and the like.

Alternative Applications of PGR

Figure 4:
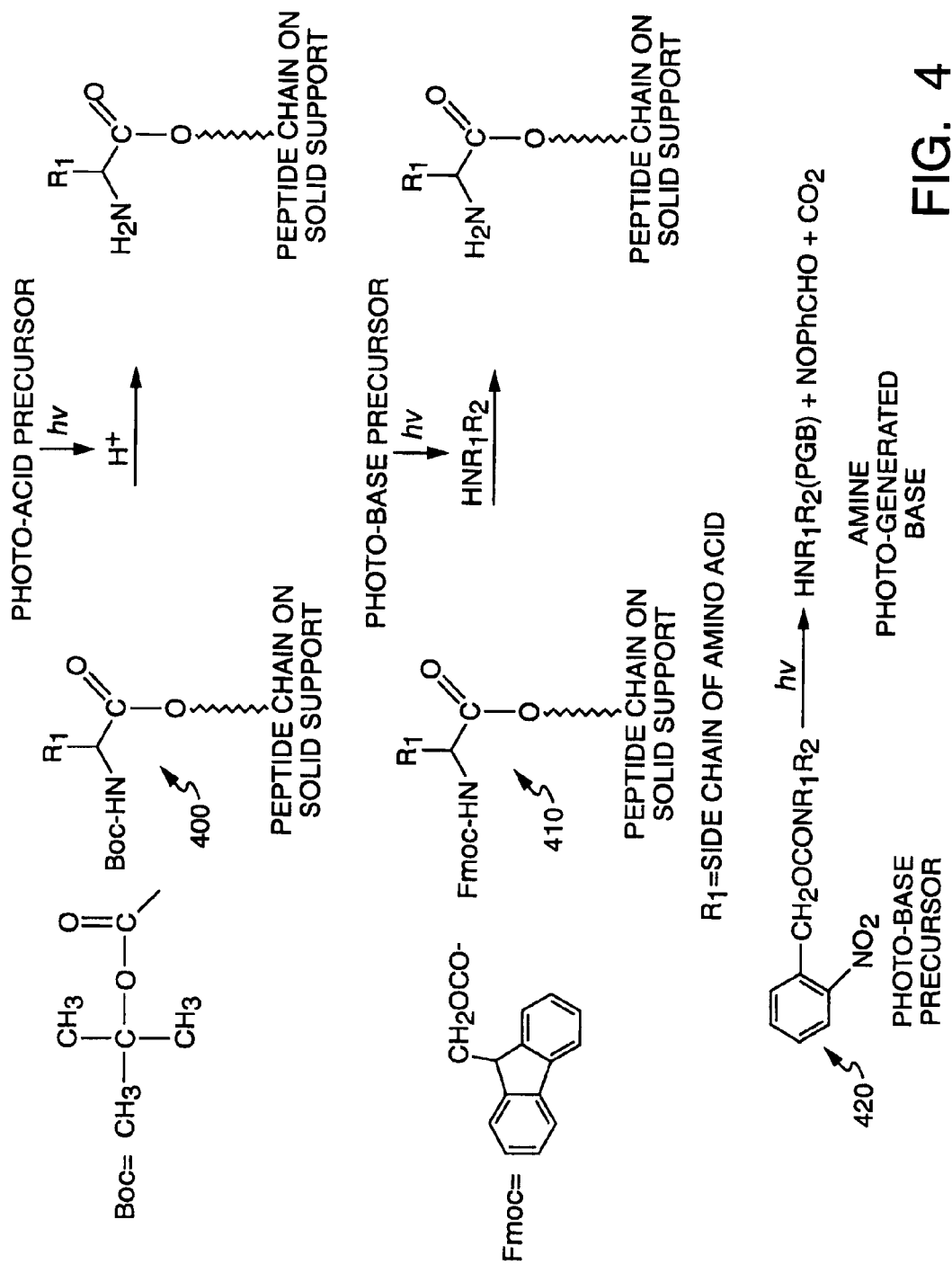
FIG. 4 is a drawing of amino acid deprotection using photo-generated acids or photo-generated bases. Boc=butyloxylcarbonyl; Fmoc=fluoroenylmethyloxycarbonyl.
Figure 5:
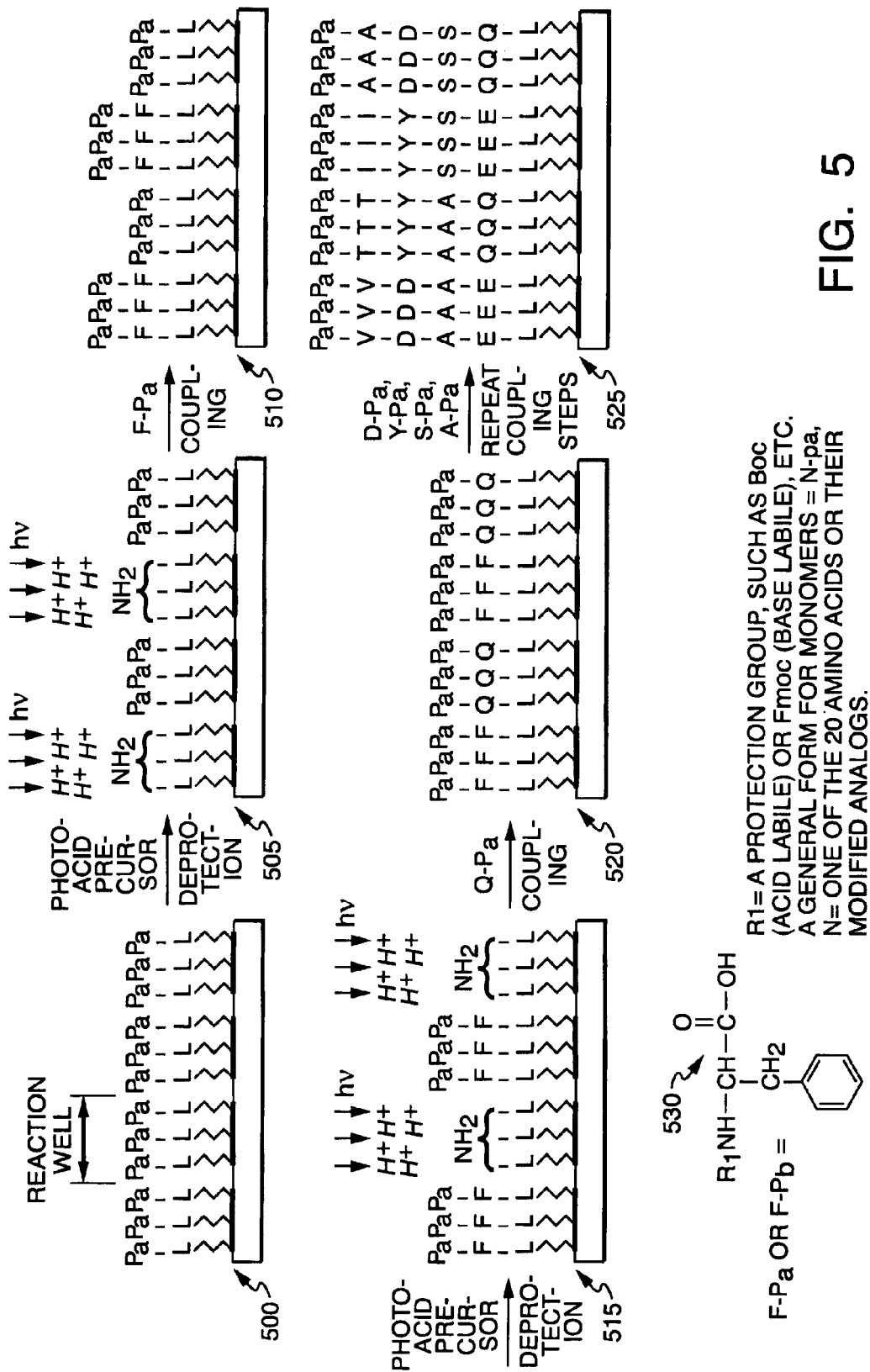
FIG. 5 is a drawing of peptide synthesis using photo-generated acids. L—linker group; $P_a$—acid-labile protecting group; F, Q, D, Y, S, and A—representative Boc-protected amino acids; hv—light exposure. In this Figure, SEQ ID NOS:2-5 are shown.

In one embodiment of the present invention, photo-generated reagents (Table 1) are applied to on-chip parallel synthesis of peptide arrays using amino acid monomers containing reactive functional groups protected by t-Boc (acid labile) or Fmoc (base labile) groups (FIG. 4). The methods of peptide synthesis are known, Sterwart and Young, "Solid phase peptide synthesis", Pierce Chemical Co.; Rockford, Ill. (1984); Merrifield, *Science* 232, 341-347 (1986); Pirrung et al., U.S. Pat. No. 5,143,854 (1992). According to one embodiment of the present invention, linker molecules are attached to a substrate surface on which peptide sequence arrays are to be synthesized. Each linker molecule contains a reactive functional group, such as an —NH$_2$ group, protected by the acid labile t-Boc group 500. Next, a photo-acid precursor or a photo-acid precursor and its photosensitizer are applied to the substrate. A predetermined light pattern is then projected onto the substrate surface 505. At the illuminated sites, acids are produced, the acid labile protecting groups, such as t-Boc, are cleaved from the N-terminal NH$_2$ thereby enabling it to react with incoming monomers (FIG. 4). At the dark sites, no acid is produced and, therefore, the acid labile protecting groups of the linker molecules remain intact. The substrate surface is then washed and subsequently supplied with the first monomer (a protected amino acid, its analogs, or oligomers), which adds only to the deprotected linker molecules under conventional coupling reaction conditions 510. A chemical bond is thus formed between the NH$_2$ group of the linker molecules and the carbonyl carbon of monomers to afford an amide linkage. After proper washing steps, the addition of the first residue is complete. The attached amino acid monomer also contains a reactive functional group protected by the acid labile t-Boc group. The substrate containing the arrays of the growing sequences is then supplied with a second batch of a photo-acid precursor and exposed to a second predetermined light pattern 515. The selected sequences are deprotected and the substrate is washed, and supplied, subsequently, with the second monomer. Again, the second monomer propagates only at the surface sites that have been exposed to light. The second residue added to the growing chain also contains a reactive functional group protected by an acid-labile group 520. This chain propagation process is repeated until polymers of desired lengths and chemical sequences are formed at all selected surface sites 525. For a chip containing a peptide array of any designated sequence pattern, the maximum number of reaction steps is 20×n, where n is the chain length and 20 is a constant, the number of naturally occurring amino acids. Arrays containing modified amino acids may require more than 20×n steps.

Figure 6:
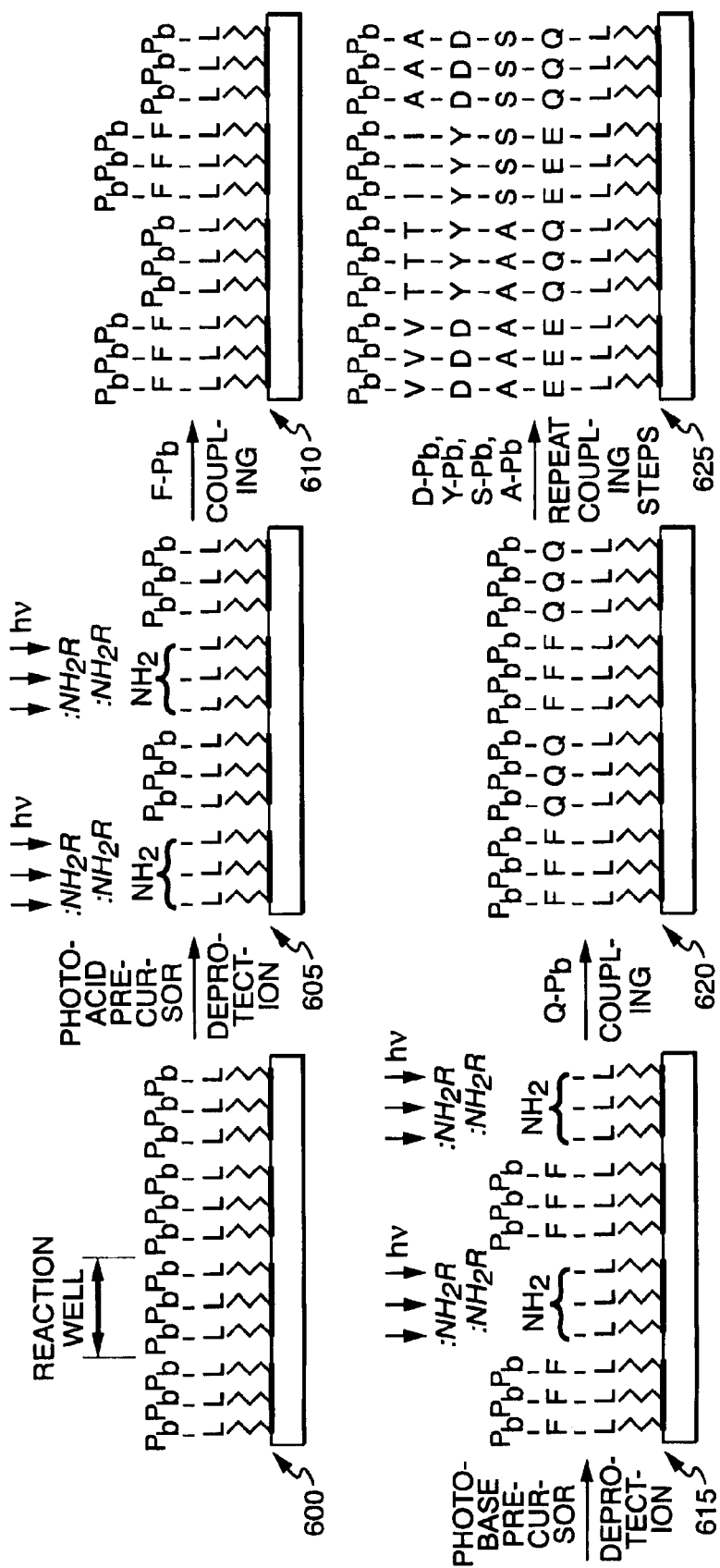
FIG. 6 is a drawing of peptide synthesis using photo-generated bases. L—linker group; $P_b$—base-labile protecting group; F, Q, D, Y, S, and A—representative Fmoc-protected amino acids; hv—light exposure. In this Figure, SEQ ID NOS:2-5 are shown.

In another preferred embodiment of the present invention (FIG. 6), a photo-base precursor, such as an amine protected by a photo-labile group, is applied to solid surface loaded with linkers 600. Each linker molecule contains a reactive functional group, such as $NH_2$, protected by a base-labile group. Next, a photo-base precursor, such as (((2-nitrobenzyl)oxy)carbonyl)-piperidine (Cameron and Fréchet, J. Am. Chem. Soc. 113, 4303-4313 (1991))[8], is applied to the substrate. A predetermined light pattern is then projected onto the substrate surface 605. At the illuminated sites, bases are produced, causing cleavage of the base-labile protecting groups from the linker molecules, and the terminal $NH_2$ groups are free to react with incoming monomers. At the dark sites, no base is produced and, therefore, the base labile protecting groups of the linker molecules remain intact. The substrate surface is then washed and subsequently supplied with the first monomer containing a carboxylic acid group, which adds only to the deprotected linker molecules under conventional coupling reaction conditions to afford an amide linkage 610. After proper washing, the addition of the first residue is completed. The attached amino acid monomer also contains a reactive functional terminal group protected by a base-labile group. The substrate containing the arrays of the growing sequences is then supplied with a second batch of a photo-base precursor and exposed to a second predetermined light pattern 615. The selected sequences are deprotected and the substrate is washed, and subsequently supplied with the second monomer. Again, the second monomer propagates only at the surface sites that have been exposed to light. The second residue added to the growing sequences also contains a reactive functional terminal group protected by a base-labile group 620. This chain propagation process is repeated until polymers of desired lengths and desired chemical sequences are formed at all selected surface sites 625.

Figure 7:
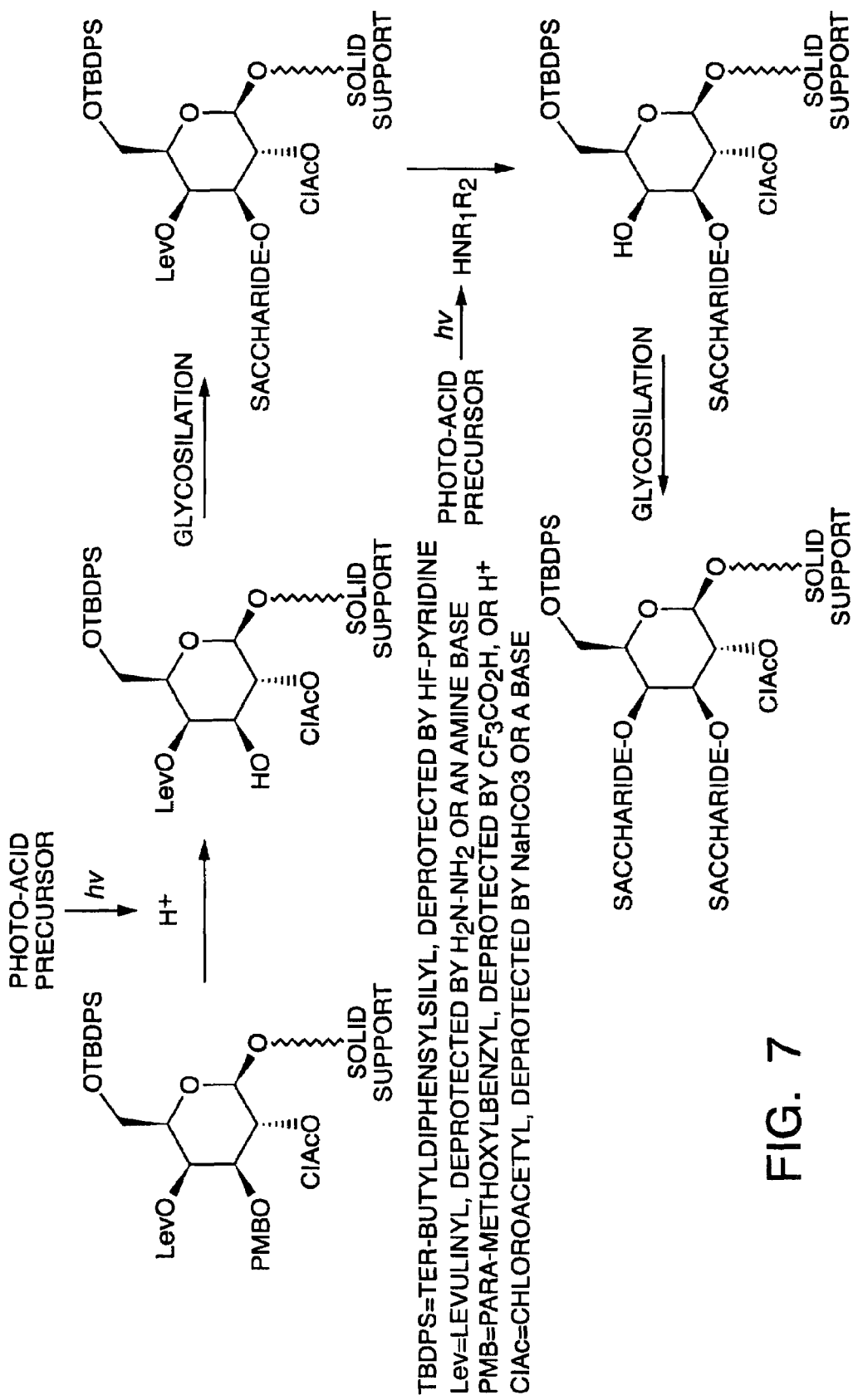
FIG. 7 is a drawing of carbohydrate synthesis using both photo-generated acids and photo-generated bases at various of reaction steps.

The present invention is not limited to the parallel synthesis of arrays of oligonucleotides and peptides. The method is of general use in solid phase synthesis of molecular arrays where complex synthesis patterns are required at each step of chain extension synthesis. One specific example is synthesis of oligosacchride arrays containing sequences of diverse carbohydrate units and branched chains (FIG. 7). According to the present invention, a photo-acid precursor is applied to a solid surface containing protected carbohydrates. Each carbohydrate molecule contains several reactive OH groups, each of which is protected by protecting groups. Each of these protecting groups requires different deprotection conditions. A predetermined light pattern is then projected onto the substrate surface. At the illuminated sites, acid is produced and the protection groups labile under a particular set of conditions are cleaved. Deprotected OH groups are free to react with an incoming molecule. At the dark sites, no acid is produced and, therefore, the acid labile protecting groups of the carbohydrate molecules remain intact. The substrate surface is then washed and subsequently supplied with a monomer (a carbohydrate or oligosaccharide), which adds only to the deprotected OH under conventional reaction conditions to afford a glycosidic linkage. Wong et al., J. Am. Chem. Soc. 120, 7137-7138 (1998). These steps are repeated to give oligosaccharides containing various glycosidic linkages at the first deprotected OH position. Next, a photo-base precursor is applied to the substrate. A second predetermined light pattern is then projected for the second time onto the substrate surface. At the illuminated sites, base is produced and the protection groups labile under this condition are cleaved. Deprotected OH groups of the second batch are free to react with an incoming molecule. At the dark sites, no base is produced and, therefore, the base labile protecting groups of the carbohydrate molecules remain intact. The substrate surface is then washed and subsequently supplied with a second monomer, which adds only to the second deprotected OH of the second time under conventional reaction conditions to afford a glycosidic linkage. These steps are repeated to give oligosaccharides containing various glycosidic linkages at the second deprotected OH position. Branched oligosaccharides are formed. In continued synthesis, various PGR are used to achieve selective deprotection of the OH protecting groups until desired oligosaccharide arrays are synthesized.

The present invention enables use of photo-generated reagents in more cases than just deprotection reactions to achieve selective reaction in accordance with a predetermined pattern without changing the course of well-developed conventional chemistry. Furthermore, the present invention is not limited to deprotection reactions, photo-generated reactive compounds, such as alcohols (ROH, R=alkyl, aryl and their substituted derivatives), can be used as reagents for a variety of chemical conversions, such as esterification, nucleophilic substitution and elimination reactions. These reactions are important steps for fabrication of custom MMA-chips.

Synthesis Apparatus

Figure 8A:
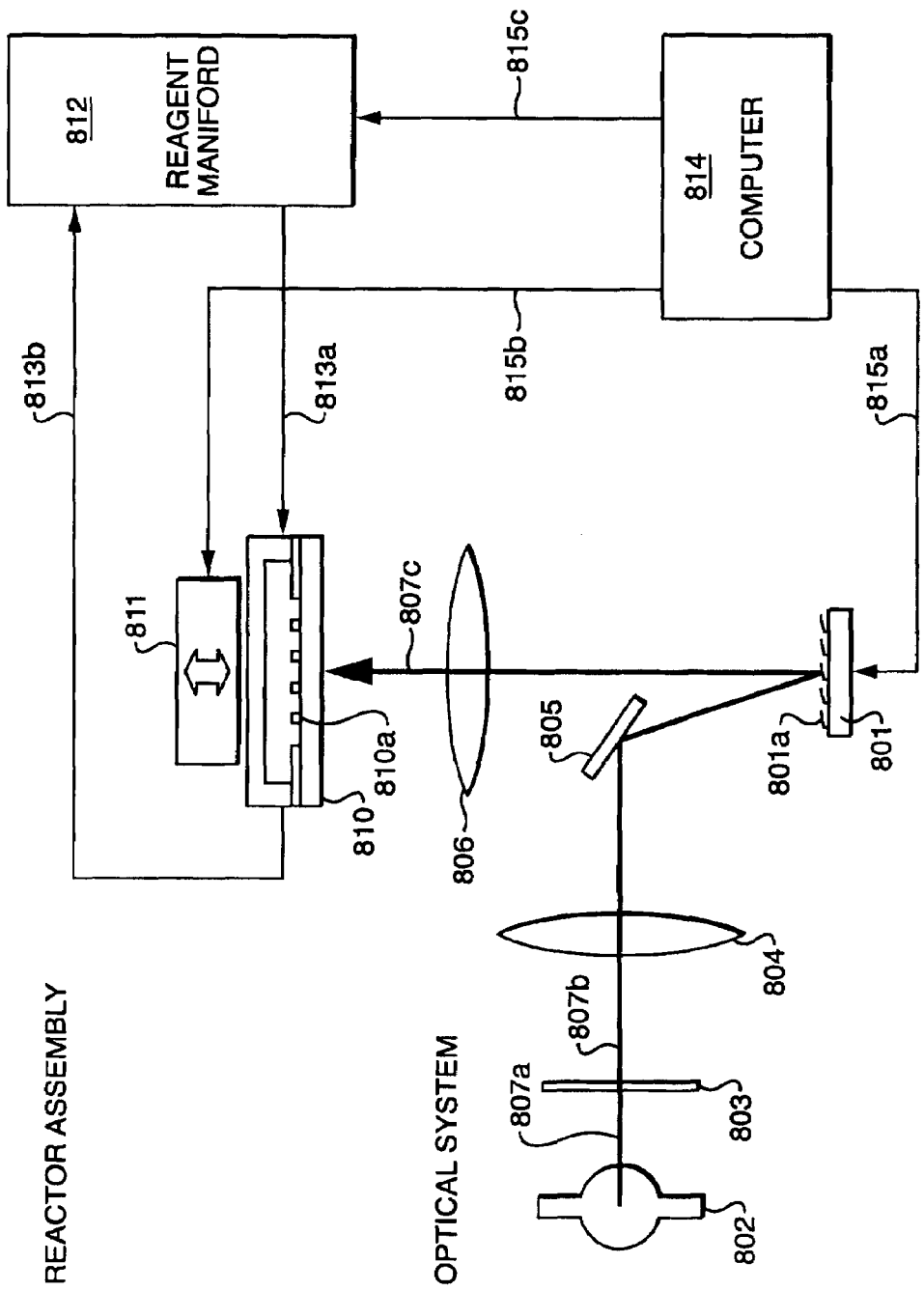
FIG. 8A is a schematic illustration of the synthesis apparatus using a micromirror array modulator.

FIGS. 8A thought 8C illustrate three embodiments of the programmable, light-directed synthesis apparatus of this invention. As shown in FIG. 8A, the apparatus is comprised of four sections: a reagent manifold 812, an optical system, a reactor assembly, and a computer 814.

Reagent Manifold

The reagent manifold 812 of FIG. 8A performs standard reagent metering, delivery, circulation, and disposal. It consists of reagent containers, solenoid or pneumatic valves, metering valves, tubing, and process controllers (not shown in FIG. 8A). The reagent manifold 812 also includes an inert gas handling system for solvent/solution transport and line purge. The design and construction of such a manifold are well known to those who are skilled in the art of fluid and/or gas handling. In many cases, commercial DNA/RNA, peptide, and other types of synthesizers can be used as the reagent manifold 812 of this invention.

Optical System

The function of the optical system shown in FIG. 8A is to produce patterned light beams or light patterns 807c for initiating photochemical reactions at predetermined locations on a substrate surface 810a. The optical system shown in FIG. 8A is comprised of a light source 802, one or more filters 803, one or more condenser lenses 804, a reflector 805, a Digital Micromirror Device (DMD) 801, and a projection lens 806. During operation, a light beam 807a is generated by the light source 802, passes through the filter(s) 803, and becomes a light beam 807b of desired wavelength. A condenser lens 804 and a reflector 805 are used to direct the light beam 807b on to the DMD 801. Through a projection lens 806, DMD projects a light pattern 807c on the substrate surface 810a of a reactor 810. Details about the DMD 801 are described below.

A light source 802 may be selected from a wide range of light-emitting devices, such as a mercury lamp, a xenon lamp, a halogen lamp, a laser, a light emitting diode, or any other appropriate light emitter. The wavelengths of the light source 802 should cover or fall within the excitation wavelengths of the concerned photochemical reaction. The preferred wavelengths for most of the concerned photochemical reactions are between 280 nm and 500 nm. The power of the light source 802 should be sufficient to generate a light pattern 807c intense enough to complete the concerned photochemical reactions in a reactor 810 within a reasonable time period. For most applications, the preferred light intensity at the substrate surface 810a position is between 0.1 to 100 mW/cm$^2$. For many applications, a mercury lamp is preferred due to its broad wavelengths and availability of various powers.

Selection criterions for a filter(s) 803 are based on the excitation wavelength of concerned photochemical reactions and other considerations. For example, it is often desirable to remove undesirably short and long wavelengths from the light beam 807a in order to avoid unwanted photo-degradation reactions and heating in a reactor 810. For example, in the synthesis of oligonucleotides and other bio-related molecules, it is preferred to remove wavelengths shorter than 340 nm. To avoid heating, an infrared cut-off filter is preferably used to remove wavelengths beyond 700 nm. Therefore, more than one filter may be needed.

A key component in the Optical System shown in FIG. 8A is a Digital Micromirror Device 801, which is used to generate light patterns 807b. A DMD is an electronically controlled display device and it is capable of producing graphical and text images in the same manner as a computer monitor. The device is commercially available from Texas Instruments Inc., Dallas, Tex. USA, for projection display applications (Hornbeck, L. J., "Digital light processing and MEMS, reflecting the digital display needs of the networked society," SPIE Europe Proceedings, 2783, 135-145 (1996)). Each DMD 801 contains a plurality of small and individually controllable rocking-mirrors 801a, which steer light beams to produce images or light patterns 807c.

DMD 801 is a preferred means of producing light patterns in the present invention for several reasons. First, it is capable of handling relatively short wavelengths that are needed for initiating concerned photochemical reactions. Second, the device has high optical efficiency. Third, it can produce light patterns of high contrast ratio. In addition, devices of high resolution formats (up to 1920×1080) have been demonstrated. These features permit one to conveniently generate optical patterns for the synthesis of practically any desired molecular sequence array by using the photochemistry described in this invention. In this aspect, the apparatus of this invention is highly flexible as compared with the prior art method of producing sequence arrays using photomasks.

Figure 8B:
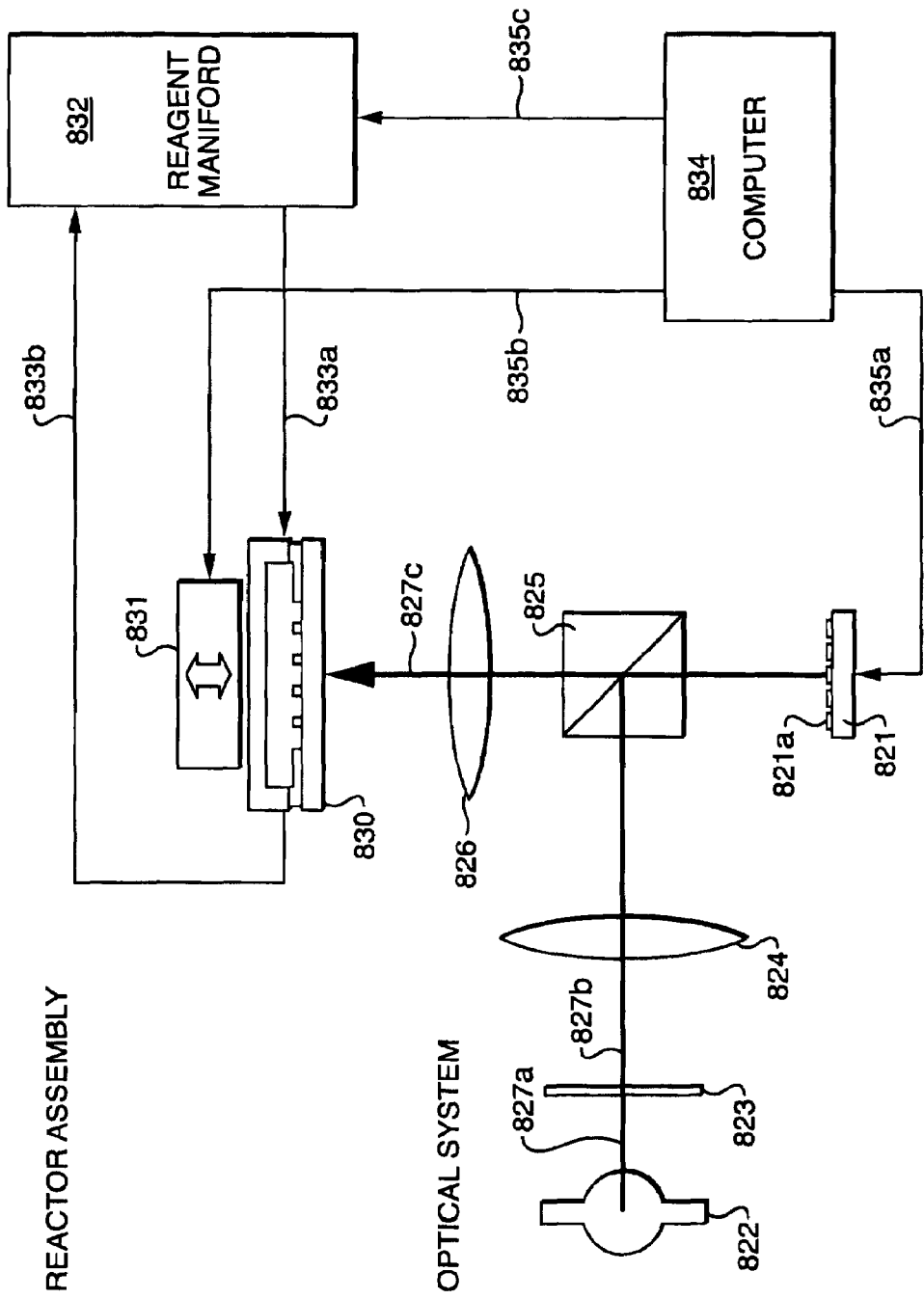
FIG. 8B is a schematic illustration of the synthesis apparatus using a reflective LCD array modulator.

Other types of electronically controlled display devices may be used for generating light patterns. FIG. 8B illustrates an exemplary embodiment of the present invention, using a reflective liquid crystal array display (LCD) device 821. Reflective LCD devices are commercially available from a number of companies, such Displaytech, Inc. Longmont, Colo. USA. Each reflective LCD device 821 contains a plurality of small reflectors (not shown) with a liquid crystal shutter 821a placed in front of each reflector to produce images or light patterns. High-resolution devices, up to 1280× 1024, are already available from Displaytech. The optical system shown in FIG. 8B is like that of the device of FIG. 8A except for the optical arrangement for directing light onto display devices. A beam splitter 825 is used in the optical system shown in FIG. 8B to effectively couple light onto and out of flat reflects.

Figure 8C:
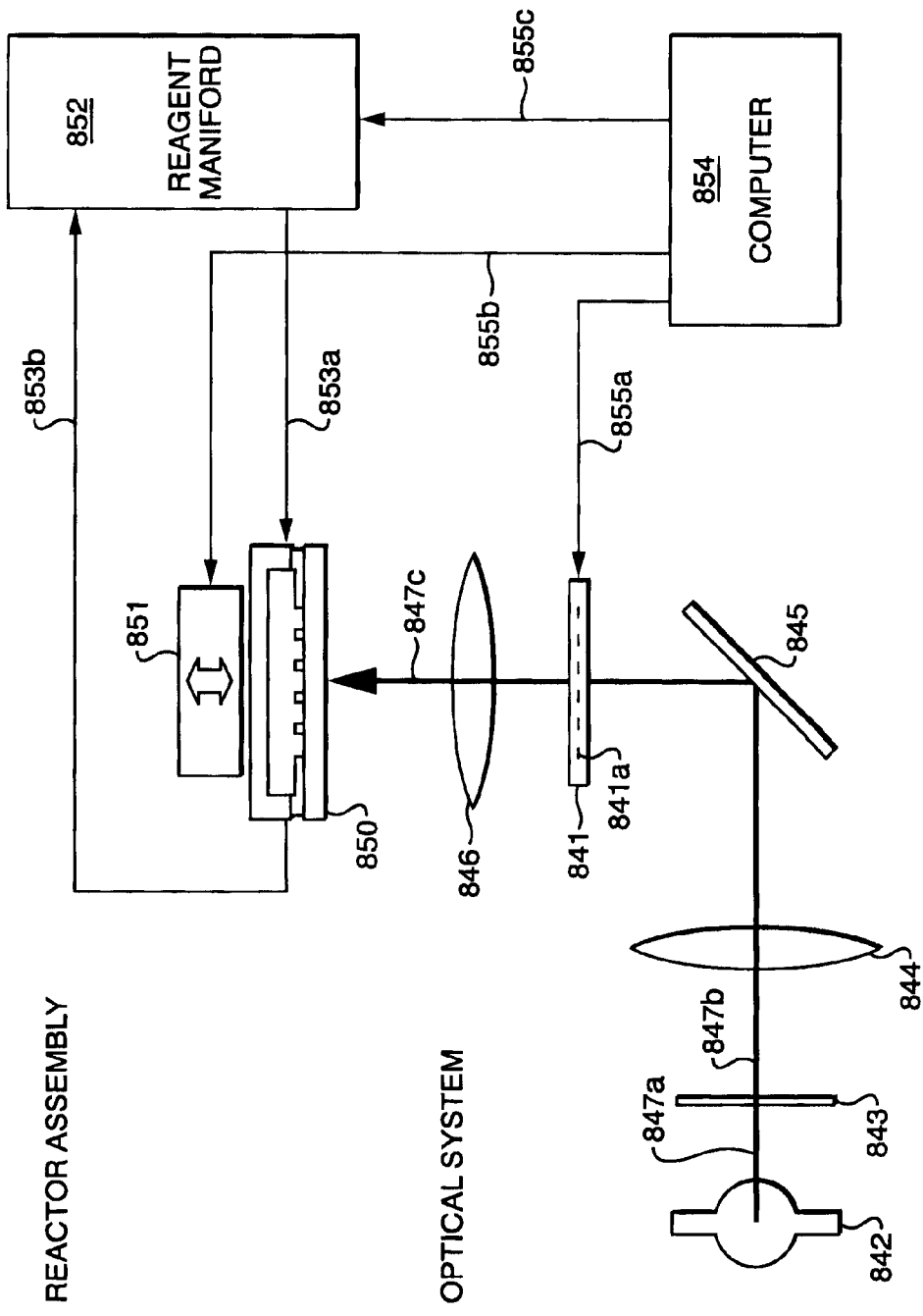
FIG. 8C is a schematic illustration of the synthesis apparatus using a transmissive LCD array modulator.

In another embodiment of the present invention, a transmissive LCD display 841 is used to generate light patterns, as shown in FIG. 8C. A transmissive LCD display 841 contains a plurality of liquid crystal light valves 841a, shown as short bars in FIG. 8C. When a liquid crystal light valve 841a is on, light passes; when a liquid crystal light valve is off, light is blocked. Therefore, a transmissive LCD display can be used in the same way as an ordinary photomask is used in a standard photolithography process (L. F. Thompson et al., "*Introduction to Microlithography*", American Chemical Society, Washington, D.C. (1994)). In FIG. 8C, a reflector 845 is used to direct a light beam 847b to the transmissive LCD display 841.

Most commercially available display devices, including DMD, reflective LCD, and transmissive LCD are designed for handling visible light (400 nm to 700 nm.) Therefore, when these commercially available display devices are used, the best operation mode of the programmable, light-directed synthesis apparatus of this invention is achieved when the excitation wavelength of the photo-reagent precursors is between 400 mm and 700 mm. However, the use of the instrument and the methods of this invention extends beyond the above wavelength range.

Figure 12:
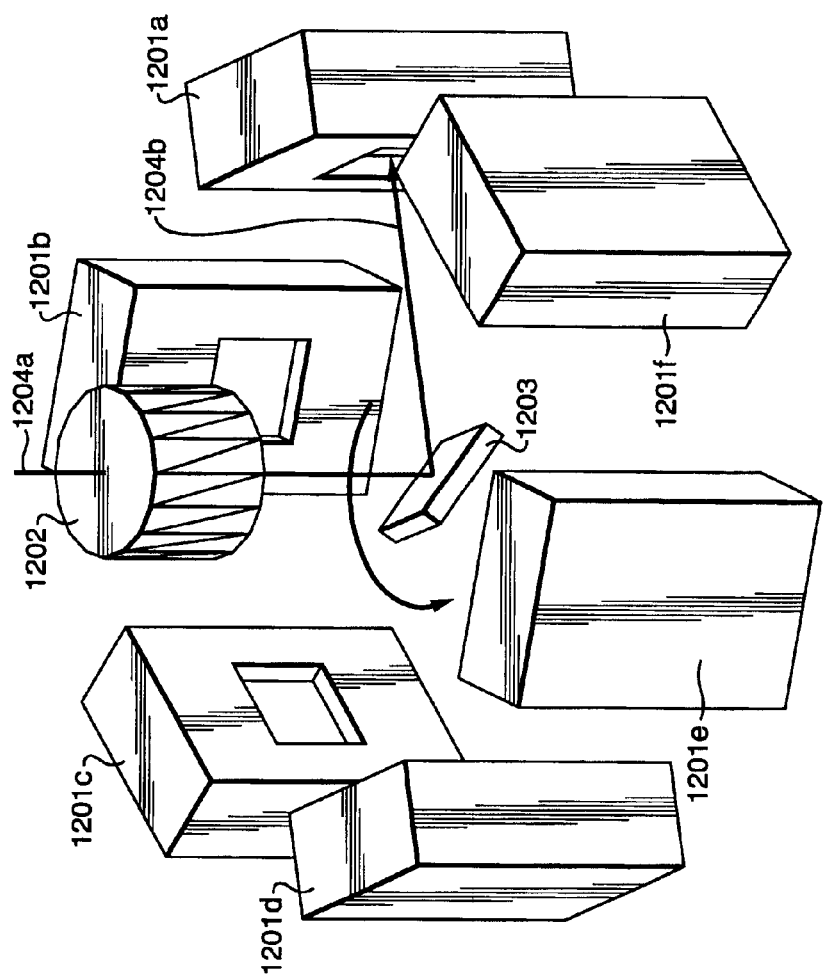
FIG. 12 illustrates a stepping mechanism for parallel synthesis of a plurality of arrays.

FIGS. 8A through 8C depict apparatus designs for making one array chip at a time. The present invention also encompasses devices for producing a plurality of chips. FIG. 12 schematically illustrates a mechanical/optical stepping mechanism for enhancing the throughput and the efficiency of the synthesis apparatus of this invention. In this stepping mechanism, a light beam 1204a is projected from a display device, (not shown in the figure,) passes through a projection lens 1202, and is directed by a reflector 1203 towards a reactor 1201a forming an image or a light pattern 1204b. The reflector 1203 has a rotating mechanism that can direct the light pattern 1204b towards any one of the several surrounding reactors 1201a through 1201f. In a regular synthesis process of, for example, oligonucleotides, the light pattern 1204b is directed towards a specific reactor, e.g. 1201a, only during a photochemical deprotection reaction step. Then the light pattern 1204b is directed towards other reactors, while reactor 1201a goes through the rest of synthesis steps, such as flushing, coupling, capping, etc.

Other stepping mechanisms may also be used in the present invention. For example, a step-and-repeat exposure scheme, which is routinely used in photolithography of semiconductors, may be used. General descriptions of step-and-repeat photolithography were given by L. F. Thompson et al., in *Introduction to Microlithography*, American Chemical Society, Washington, D.C. (1994). In this scheme, a large substrate containing multiple reaction-well arrays is used. The substrate is mounted on a x-y translation stage. At each step, an optical exposure covers one or several arrays. Then, the substrate is moved to the next position and another optical exposure is performed. The process is repeated until all reaction-well arrays are exposed.

The present invention is not limited to the use of electronically controlled display devices as the means of generating photolithography patterns. Conventional photomasks, which are made of glass plates coated with patterned chromium or any other appropriate films, may be used as well. In this case, the transmissive LCD display device 841 shown in FIG. 8C is replaced with a conventional photomask while rest of the apparatus remains the same. The use of conventional photomasks is preferred for the production of a large number of the same products. A conventional photomask may contain a large number of array patterns so that a large number of molecular arrays can be synthesized in parallel. However, for small batch production of various different array products the use of electronically controlled display devices is much preferred due to its flexibility.

Reactor Configuration

Figure 9A:
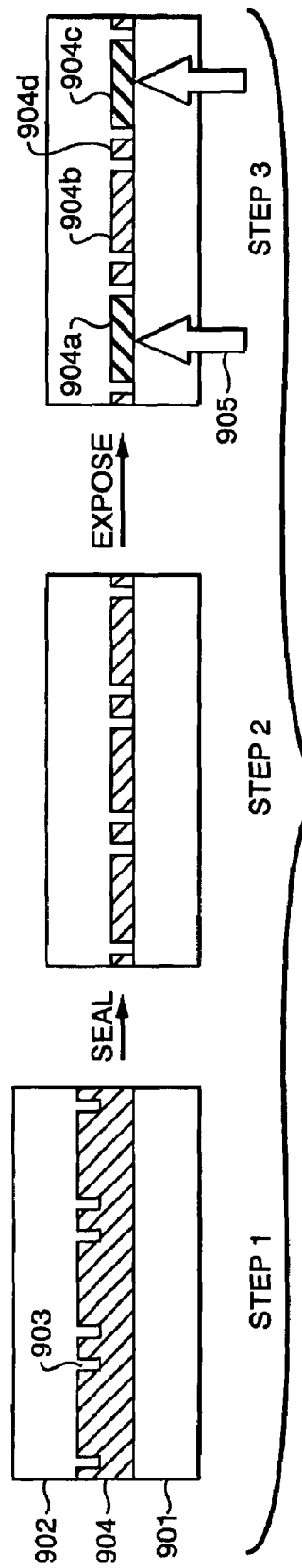
FIG. 9A illustrates an isolation mechanism using microwell structures on a back cover.
Figure 9B:
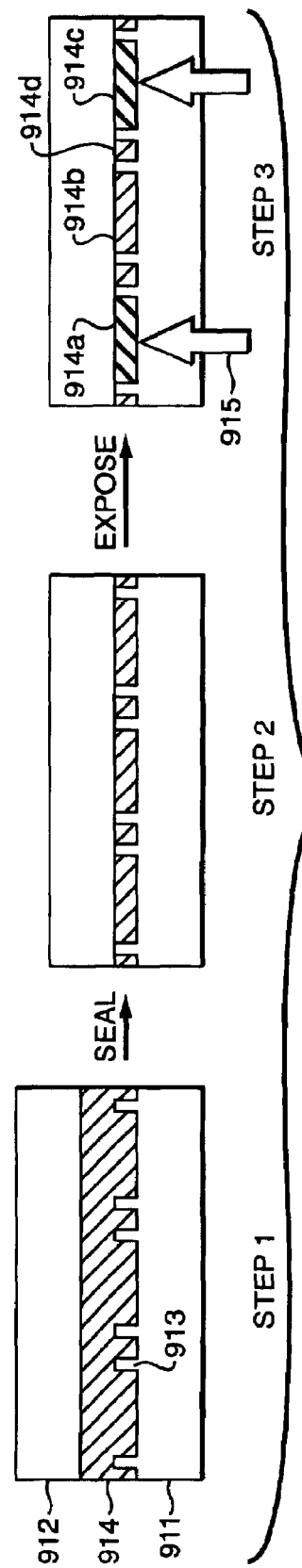
FIG. 9B illustrates an isolation mechanism using microwell structures on a substrate.

As described in earlier sections, photogenerated reagents involved in the current invention are in solution phase. When the reagents are used to produce spatially defined patterns, such as arrays, appropriate measures should be taken to spatially isolate individual elements. FIGS. 9A through 9C schematically illustrate three preferred embodiments of isolation mechanisms of the present invention. In the embodiment shown in FIG. 9A, a transparent substrate 901 and a cap 902 form a reaction cell or a reactor, which is filled with a solution containing one or more photo-reagent precursors. Reaction-wells, bounded by barriers 903, are embossed on the cap 902. The cap 902 is preferably made of a plastic or an elastomer material inert to all chemicals involved in the reaction. Before a photolytic reaction takes place, the cap 902 is pushed against the substrate 901 forming contacts between the barriers 903 and the substrate and isolates of individual reaction-wells. Light beams are then projected into a number of selected reaction-wells 904a and 904c, as shown in Step 3 of FIG. 9A. Photolytic and other photo-reagent-induced reactions take place in the light-exposed reaction-wells 904a and 904c while there is no photo activate reaction in the unexposed reaction-well 904b. When properly constructed and operated, the isolation mechanism described prevents diffusion of reagents across individual reaction-wells. In addition, the space between adjacent reaction-wells 904b and 904c provides a buffer zone 904d to further prevent any intermixing between reaction-wells.

Figure 10A:
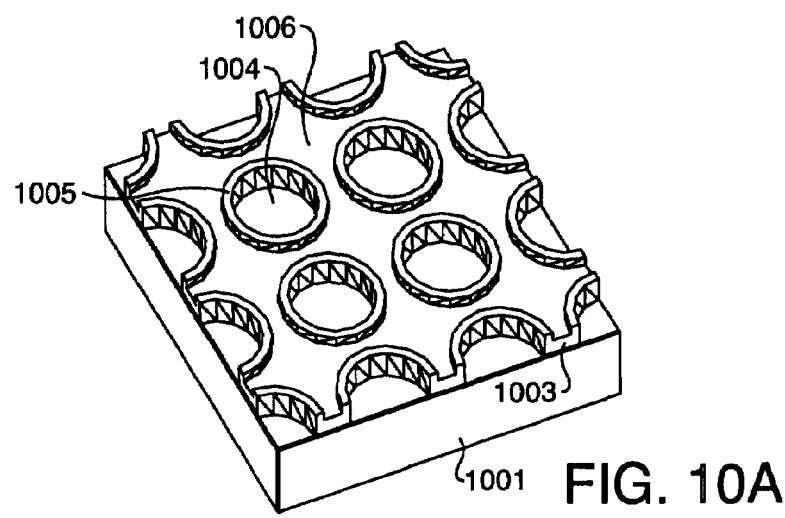
FIG. 10 is an exploded schematic of a reactor cartridge and an enlarged view of reaction-wells.
Figure 10:
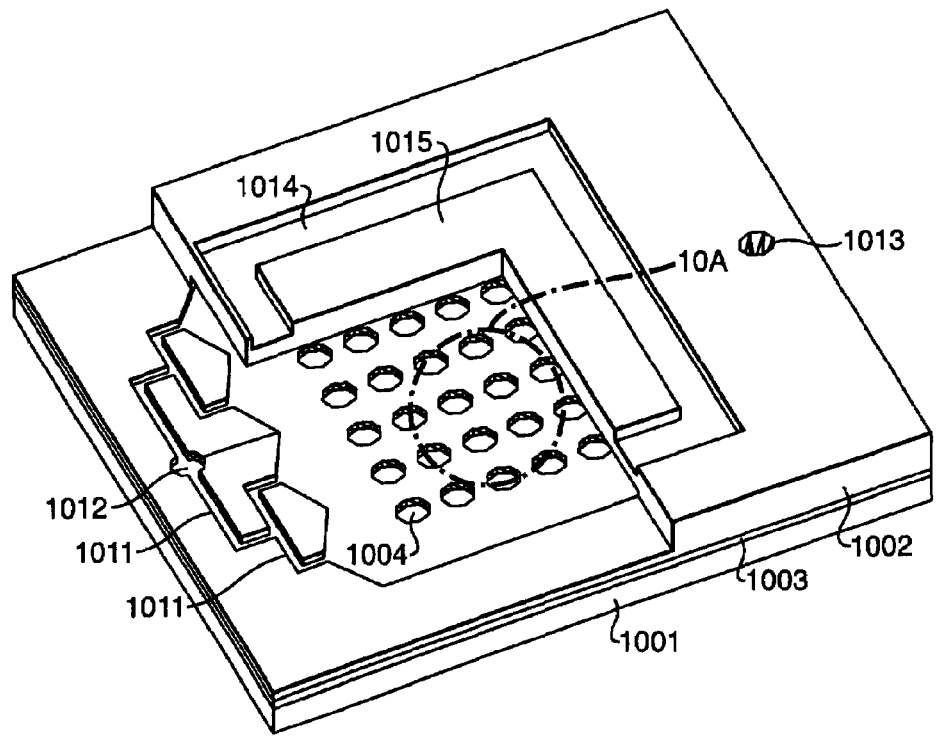

The buffer zone 904d, shown in FIG. 9A, provides space for addition mechanisms of preventing interference among individual reaction-wells. FIG. 10 illustrates detailed structure of the reaction-wells of the current invention in a three-dimensional perspective view. The figure shows that the buffer zones (labeled as 1006 in FIG. 10) are all interconnected. This interconnected structure permits one to flush the buffer zone with appropriate solutions while all the reaction-wells are closed. In are preferred method, buffer zone 904d is flushed after the completion of the photolytic and photo-reagent-induced reactions and before the lifting of the cap 902, with a solution that would either quench the photo-reagent-induced chemical reactions or neutralize the photo-generated reagents inside the exposed reaction-wells 904a and 904c. The spillover of the photogenerated reagents from the exposed reaction-wells 904a and 904c would thus not cause no undesirable chemical reactions in other areas after the cap 902 is lifted. For neutralizing a photogenerated acid, a weak basic solution, such as pyridine in $CH_2Cl_2$, may be applied. For quenching nucleotide-coupling reaction, acetonitrile or other suitable solvents may be used.

FIG. 9B illustrates another embodiment of the isolation mechanism of the present invention. In this embodiment, reaction-well structures, or reaction-well barriers 913, are constructed on a transparent substrate 911 while the cap 912 has a flat inner surface. The substrate 911 is preferably made of glass. The cap 912 is preferably made of a plastic or an elastomer material inert to all chemicals involved in the reactions. The seal mechanism and the preferred operation mode are similar to those described earlier for the embodiment shown in FIG. 9A.

FIG. 9C illustrates the third embodiment of the isolation mechanism of the present invention. In this embodiment, a pattern of non-wetting film 933 is coated on the surface of a transparent substrate 931. During an operation, a reactor is first filled with a solution 934. Then the solution 934 is drained from the reactor and droplets are formed on the substrate 931 surface because the solution wets the substrate 931 surface but not the non-wetting film 933 surface. The droplets are isolated from each other. Light beams 935 can then be projected onto predetermined droplets 934a and 934c to initiate photolytic and other photo-reagent-induced reactions. This embodiment eliminates the need for a sealing mechanism and is suitable for large-scale biochip production using large substrates. The use of non-wetting films to confine fluid is well-known in the art and has been described by Thomas M. Brennan in U.S. Pat. No. 5,474,596 for the synthesis of DNA oligomers using an inkjet-printing method.

Reactors of this invention are preferably assembled into a cartridge form as illustrated in FIG. 10. The design shown in the figure utilities the isolation mechanism shown in FIG. 9B. Other isolation mechanisms, such as the ones shown in FIGS. 9A and 9C, can be easily implemented into similar cartridge forms. As shown in FIG. 10, each cartridge contains a transparent substrate 1001, which can be made of glass or polymer materials of suitable chemical and optical properties. Above the substrate is a barrier layer 1003 containing pluralities of openings to form arrays of isolated reaction-wells 1004. In principle, the reaction-wells can be of any reasonable shapes and sizes. Circular and square wells are preferred. Most preferably, wells are of circular shape of 10 to 1,000 μm in diameter and 5 to 100 μm in depth. For example, in a specific design, circular reaction-wells are 140 μm in diameter, 20 μm in depth, and are arranged as an orthogonal array with equal center-to-center distance of 200-μm. With this design, 2,500 reaction-wells are packed into an area of one square centimeter. In each reaction well, about 6.4 fmol molecules may be synthesized, assuming the average distance between immobilized adjacent molecules is 20 Å. The volume of the reaction-well is about 300 pico-liter, providing sufficient volume required for reactions. The barrier layer 1003 is made of opaque materials, such as metals or blackened polymers, to optically isolate individual reaction-wells from each other. The third layer is a reactor cap 1002. The cap 1002 has three functions: reactor enclosure, reagent connection/distribution, and reaction-well isolation. The cap 1002 is preferably made of a polymer material that is flexible and resistant to chemicals/solvents involved in the concerned synthesis processes. The material may be selected from a group of polymers including polyethylene, polypropylene, polyethylene-polypropylene copolymer, fluorinated polymers and various other suitable ones. The reagent inlet 1012 and outlet 1013 are placed at two opposite ends of the reactor. Branching channels 1011 are made to distribute reagents evenly across the reactor. The center region of the cap is a pad 1015 that can be pushed down to tightly seal the reaction-wells 1004 below. Immediately above the reactor there is a mechanical actuator (not shown in FIG. 10 but shown in FIGS. 8A through 8C as 811, 831, and 851), which can be, for example, driven either solenoidally or pneumatically. The actuator can either push the pad of the reactor cap to seal all reaction-wells or retract to open all the reaction-wells. This operation is to accommodate the sealing mechanism shown in FIGS. 9A and 9B. The inset in FIG. 10 shows an enlarged view of the reaction-well structures, which contain extruded rims 1005 to facilitate sealing. While not shown in FIG. 10, the reactor substrate contains alignment marks, which permit the alignment of the reactor in an optical lithography system of the present invention.

The reactor cartridge shown in FIG. 10 is most suitable for use in an ordinary chemical and biochemical laboratory environment. The enclosed construction of the cartridge prevents chemical and particulate contamination from the environment. In order to achieve the best and consistent results, the cartridges are preferably manufactured in a controlled environment to ensure the chemical integrity inside the cartridge. The cartridges are then filled with an inert gas, such as Ar, and sealed by plugging the inlet and outlet of the reactor. Then the cartridges can be stored and/or shipped to user laboratories.

Reactor Fabrication

The reactors of the present invention (FIGS. 9A through 9C and 10) can be fabricated using various well-known microfabrication processes, such as photolithography, thin film deposition, electroplating, and molding (M. Madou, *Fundamentals of Microfabrication*, CRC Press, New York, (1997)). These techniques have been widely used for making various of microfluidics devices, electromechanical devices, chemical sensors, and optical micro-devices. For example, the reaction-well structure shown in FIG. 10 can be fabricated by using electroplating of suitable metal films on a glass substrate. At the end of this description, an example is given to demonstrate the fabrications processes involved. The reaction-well structures on a glass substrate may also be made using chemical etching processes, which have been widely used to make various microfluidics devices (Peter C. Simpson et al. Proc. Natl. Acad. Sci., 95: 2256-2261 (1998)).

Reactor cap 1002, shown in FIG. 10, can be fabricated using a precision molding process. Such a process is widely available in plastic fabrication industry. The polymer material used is preferably in black color to minimize light reflection and scattering during light exposure. Welding and adhesive bounding methods can be used to assemble the plastic cap 1002 and a substrate 1001 into an integrated cartridge.

Making non-wetting film patterns on glass and other substrates is a well-known art in many fields (Uthara Srinivasan et al., Proc. IEEE Solid-State Sensors and Actuators, June 1991, 1399-1402). The film is usually formed by a monolayer of self-assembled molecules (SAM) or a thin polymer film of low surface energy material such as Teflon. The most frequently used SAMs on glass substrates include various hydrocarbon alkylsilanes and fluoroalkylsilanes, such as octadecyltrichlorosiliane and 1H, 1H, 2H, 2H-perfluorodecyltrichlorosiliane. The patterning process involves the use of photoresists and photolithography. Example VII at the end of this description provides a detailed patterning procedure. Thin polymer films, such as Teflon, can be printed onto glass and plastic surfaces by using a screen printing process. The screen printing process is a well-know art in printing industry and in electronic industry. General procedures of screen printing for microfabrication applications are described by M. Madou in *Fundamentals of Microfabrication*, CRC Press, New York, (1997). In addition, hydrophobic printed slides are commercially available from vendors, such as Erie Scientific Company, Portsmouth, N.H. USA. When non-wetting film patterned substrates are used, the reactor configuration can be simplified because the reaction-well-sealing mechanisms shown in FIGS. 8A through 8C and FIG. 10 are no longer needed.

Control of the Apparatus

As illustrated in FIG. 8A, the synthesis apparatus of the present invention is controlled by a computer 814, which coordinates the actions of the DMDI) 801, the seal actuator 811 of the reactor 810, and the reagent manifold 812. In case of synthesizing oligonucleotides, during most of synthesis steps, the synthesis apparatus operates as a conventional synthesizer and the computer 814 controls reagent manifold 812 to deliver various reagents to the reactor 810. At a photo-directed deprotection step, the reagent manifold 812 delivers a photo-acid precursor into the reactor 810. The computer 814 activates the seal actuator 811 to isolate reaction-wells and, then, sends data to DMD 801 to project a light pattern 807c onto the reactor 801. At the completion of the photoreactions, the light pattern 807c is switched off, a quenching solution is delivered into the reactor 801, the seal actuator 811 is lifted, and the synthesis control system resumes the steps of conventional synthesis.

Variations and Modifications

Figure 2:
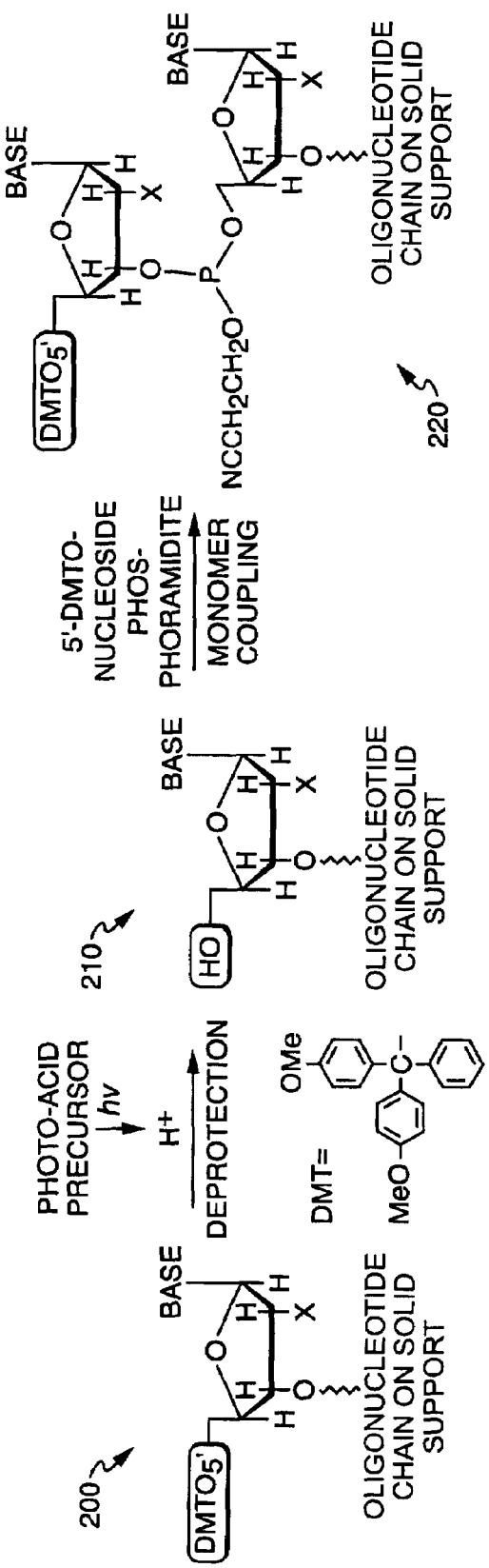
FIG. 2 is a drawing of the deprotection process using photo-generated acids in oligonucleotide synthesis.
Figure 11A:
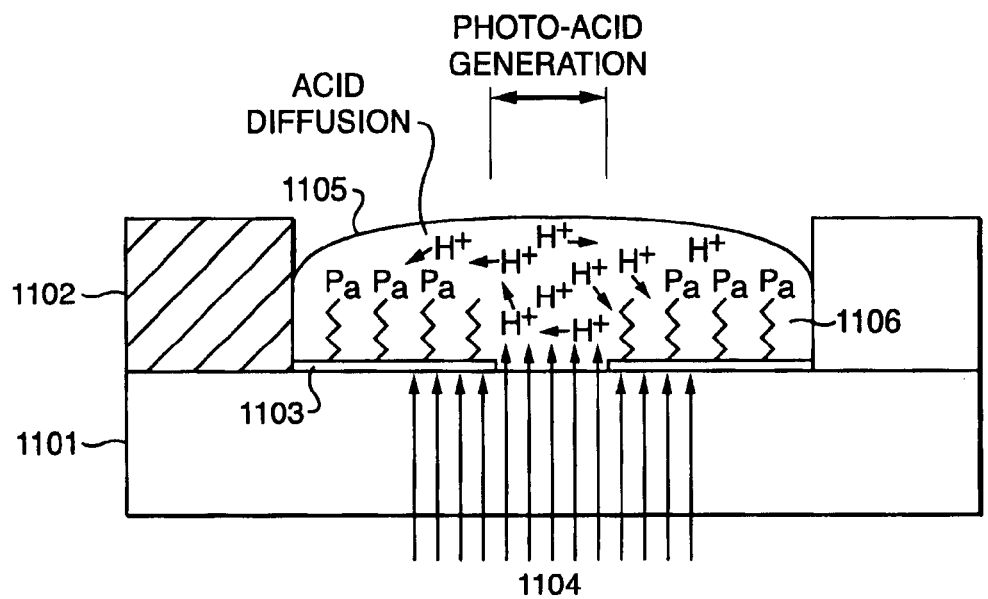
FIG. 11A is a schematic illustration of the deprotection reaction in a partially masked reaction-well.

Many variations and applications of the present invention are possible. FIG. 1 IA illustrates a variation of reaction-well structure. A mask layer 1103 is added to the bottom of the reaction well. One or more openings, which occupy a total one tenth to one half of the reaction-well surface area, are made on the masks for light 1104 to pass through. The mask layer 1103 is preferably made of a thin and chemical resistant metal film, such as Cr. On top of the metal film, a $SiO_2$ film (not shown) is deposited to facilitate immobilization of linker molecules. This reaction-well design permits the spatial separation of a photochemical reaction and photogenerated-reagent-induced chemical reactions. FIG. 11A illustrates a photo-acid induced chemical reaction. Upon a light exposure, protons $H^+$ are produced from a photo-acid precursor in the open areas. The protons, then, diffuse into surrounding areas in the well to cleave acid-labile protecting groups $P_a$ on immobilized oligomer molecules 1106. This arrangement helps to minimize the contact between photo-generated radical intermediates and the oligomers and thus, to suppress undesirable side-reactions that might occur due to the presence of radical intermediates.

Figure 11B:
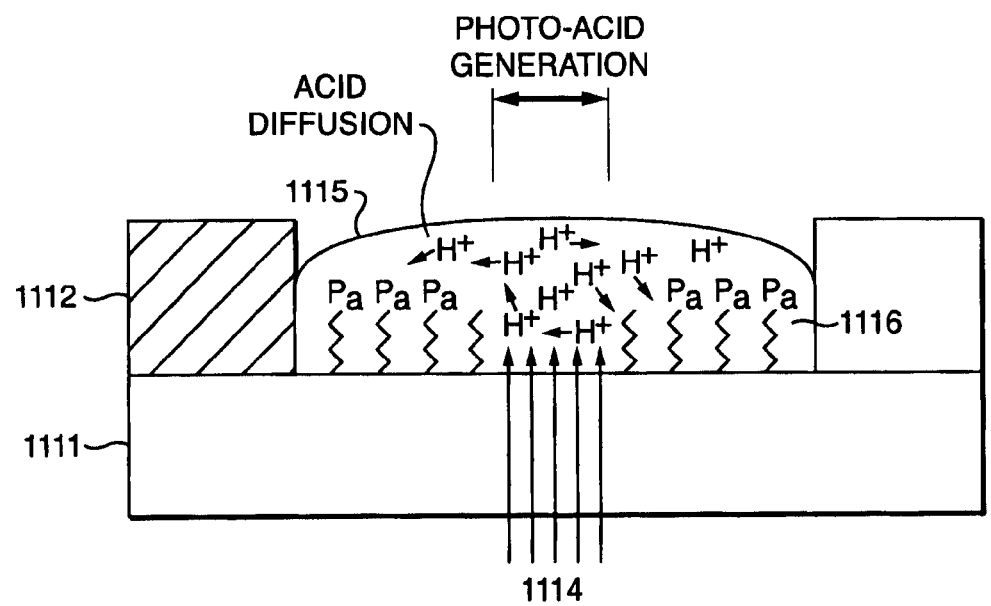
FIG. 11B is a schematic illustration of the deprotection reaction with a reaction-well being partially exposed.

FIG. 11B illustrates another variation of the reaction-well structure and light exposure strategy. This embodiment is also designed to decrease the possibility of undesirable side-reactions due radical intermediates. Only a fraction of the reaction-well surface is exposed to light 1114. The chance for undesirable side-reactions in other areas is, consequently, decreased.

The applications of the chemical processes and the apparatus (FIGS. 8A through 8C) of the present invention extend beyond the fabrication of molecular arrays. For example, the apparatus using DMD 801 shown in FIG. 8A may be used as a general-purpose assay apparatus for studying chemical and biochemical reactions. The Digital Micromirror Device 801 controls precisely and simultaneously light dosages in all individual reaction-wells of a reactor 810. This feature allows one to precisely control the production of photogenerated reagent in all reaction-wells and, therefore, to perform a large-scale, parallel assay.

Obviously many modifications and variations of this invention are possible in the light of the above teachings. It is therefore to be understood that within the scope of the appended claims the invention may be practiced otherwise than as specifically described.

The invention is further described by the following Examples, which are provided for illustrative purposes only and are not intended nor should they be construed as limiting the invention in any manner. Those skilled in the art will appreciate that variations on the following Examples can be made without deviating from the spirit or scope of the invention.

EXAMPLE I

Photo-Acid Generation

This experiment demonstrates efficient generation of $H^+$ upon light irradiation of a PGA as monitored by increased values of the chemical shift of the $H_2O$ signal as a function of light irradiation time.

Six samples containing a sulfonium salt (0.4% of 50% triaryl sulfonium hexafluorophosphate in propylene carbonate, Secant Chemicals, Boston, Mass.) in 0.5 mL $CD_2Cl_2$ were placed in nuclear magnetic resonance (NMR) tubes. A reference one-dimensional (ID) spectrum of these samples was recorded (600 MHz NMR spectrometer, Bruker, Karlsruhe, Germany) using method well known to those skilled in the art. One of the samples was then irradiated using a collimated light source (22 mW, Oriel, Stanford, Calif.) at 365 nm for a defined length of time (FIG. 13) and 1 D NMR spectrum was recorded immediately after the irradiation. A second sample was then irradiated at 365 nm for a second defined length of time (FIG. 13) and 1 D NMR spectrum was recorded immediately after the irradiation. These experiments were repeated for each of the samples prepared. For each NMR spectrum, chemical shift of the $H_2O$ was measured. In the absence of light, $H_2O$ signal appeared at 1.53 ppm. Upon irradiation, this signal moved to a higher ppm value (down field shifted) due to the generation of $H^+$.

Figure 13B:
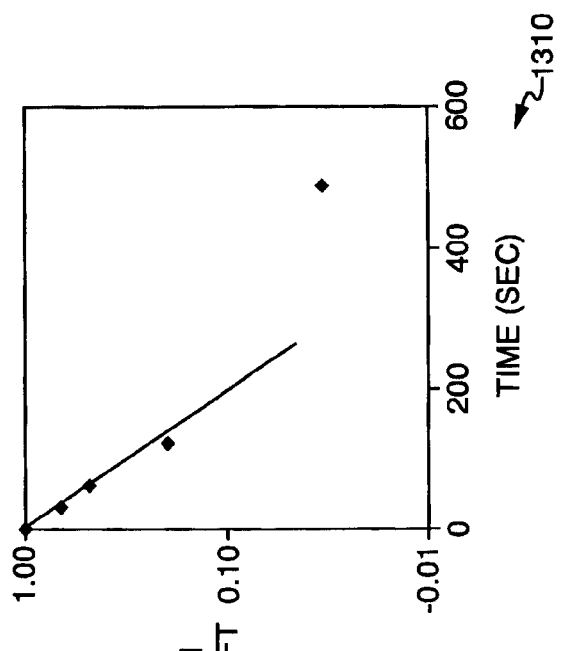
FIG. 13 is a plot of $H_3O^+$ chemical shift (ppm) versus light irradiation time (min) measured from a sample containing a photo-acid precursor.
Figure 13A:
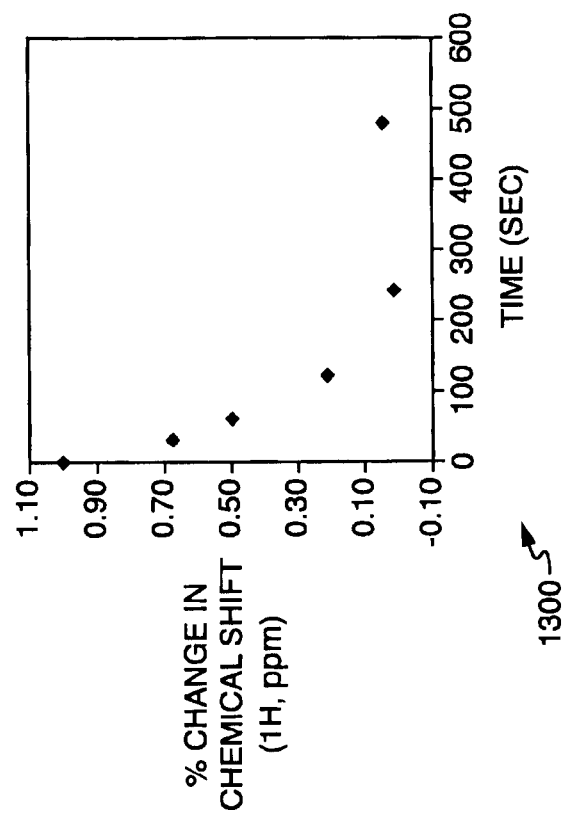

In FIG. 13 the correlation of the changes in chemical shift of the $H_2O$ signal with irradiation time is plotted. The formation of $H^+$ under the conditions used follows a first order kinetics relationship and the apparent rate constant for formation of $H^+$ derived is $1.3 \times 10^{-2} \pm 0.06$ $s^{-1}$.

EXAMPLE II

Deprotection of Nucleotide Monomers Using PGA

These experiments demonstrate efficient deprotection of the DMT group on 5'-OH of nucleosides using PGA.

Two samples were prepared in which DMT-G attached to (controlled porous glass, 0.2 µmol (CPG) added to sulfonium salt (0.4% of 50% triaryl sulfonium hexafluorophosphate in propylene carbonate, Secant Chemicals, Boston, Mass.) in 0.5 mL $CH_2Cl_2$. One sample was irradiated using a UV lamp (UVGL-25, 0.72 mW) at 365 nm for 2 min, while the other sample, a control, was ot irradiated Upon completion of the irradiation, CPG was washed with $CH_2Cl_2$ and $CH_3CN$, followed by treatment with concentrated aqueous $NH_4OH$ (1 mL) for 2 h at 55° C. The solution was briefly evaporated in vacuo. A buffer solution (0.1 M triethylammonium acetate (TEAA), 15% in $CH_3CN$) was added to the CPG sample and the resultant solution was injected into a C18 reverse phase (10 µm, µ-bondapak, Waters) HPLC column. A gradient of 0.1 M TEAA in $CH_3CN$ was used to elute the sample. Authentic samples of DMT-dG and dG were used as reference and co-injection of PGA deprotected dG and authenic dG confirms the result of the PGA reaction. 1400 and 1410 of FIG. 14A show HPLC profiles of DMT-dG and the PGA deprotected dG.

Figures 14A, 14B:
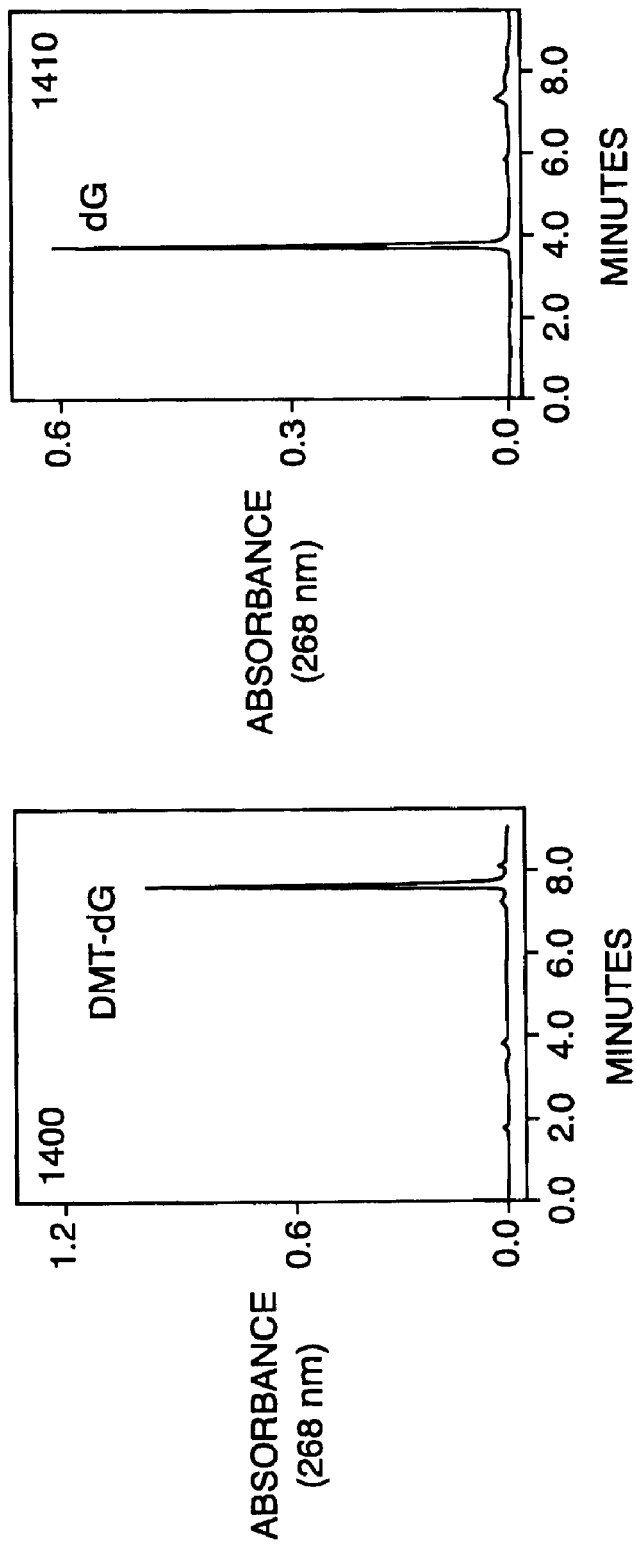
FIG. 14 shows the HPLC profiles of DNA (FIG. 14A) and RNA (FIG. 14B) nucleosides deprotected using a photo-generated acid.
Figures 14C, 14D:
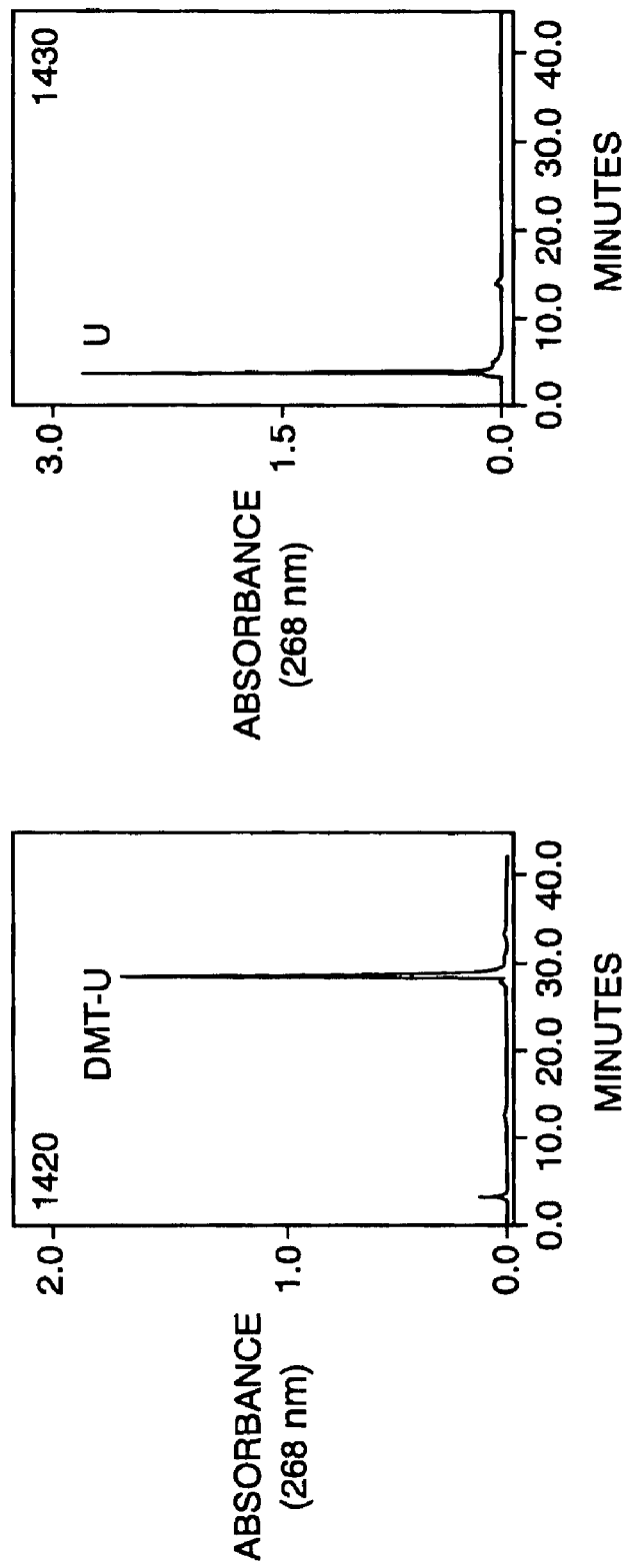

The same procedures were performed for DMT-dC, DMTAG, DMT-dA, and DMT-rU. 1420 and 1430 of FIG. 14B show HPLC profiles of DMT-rU and the PGA deprotected rU.

Other photo-acid precursors, such as 2,1,4-diazonaphthoquionesulfonate triester, triaryl sulfonium hexafluoroantimonate and hexafluorophosphate (Secant Chemicals, Boston, Mass.), and perhalogenated triazine (Midori Kagaku), were also used for these deprotection reactions. Complete deprotection of the DMT group was achieved with these phot acid precursors.

EXAMPLE III

Deprotection of Nucleoside Monomers Using Pre-Activated PGA

This experiment demonstrates that pre-activation of PGA precursor is an effective means of reducing side reactions in deprotection using PGA. Depurination due to cleavage of glycosidic bonds in nucleotides under acidic conditions is a known problem. This problem is exacerbated in the use of PGA for deprotection since at the initiation of reaction, the amount of $H^+$ requires time to build up. The following experiment is to show that this problem can be alleviated using a pre-activated PGA.

The samples and experimental conditions used in this experiment were as described in Example II, except that the PGA solution (0.4% of 50% triaryl sulfonium hexafluoroantimonate in propylene carbonate) was first irradiated at 365 nm for 2 min. before adding the CPG attached DMT-nucleoside.

Pre-irradiation (UVGL-25, 0.72 mW) at 365 nm for 2 min was perform using a PGA solution (0.4% of 50% triaryl sulfonium hexafluoroantimonate in propylene carbonate). The irradiated solution was then added to powder DMT-dA (approximately 1 µmol). The solution was incubated for an additional 2 min. 1 D NMR spectrum was recorded using methods well known to those skilled in the art. Another sample of DMT-dA (1 µmol) was mixed with a PGA solution (0.4% of 50% triaryl sulfonium hexafluoroantimonate in propylene carbonate) and the mixture was irradiated (UVGL-25, 0.72 mW) at 365 nm for 2 min. 1 D NMR spectrum was recorded. Depurination causes gradual disappearance of the signals of dA. The comparison of the two NMR spectra recorded for these experiments indicates less side reactions for the reaction using pre-activated PGA.

EXAMPLE IV

Oligonucleotide Synthesis Using PGA

These experiments demonstrate efficient synthesis of oligonucleotides on CPG support using PGA. Oligonucleotides of various sequences (A, C, G, and T) and chain lengths (n=2–8) were synthesized using photo-acid precursors on a Perspective synthesizer (Perspective Biosystems, Framingham, Mass.).

Figure 15B:
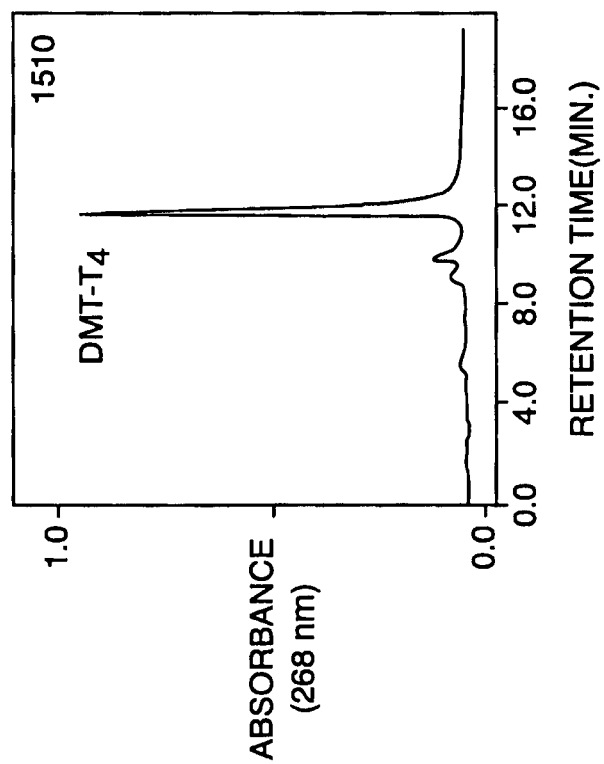
FIG. 15 shows the HPLC profiles of DNA oligomers synthesized using a photo-generated acid.
Figure 15A:
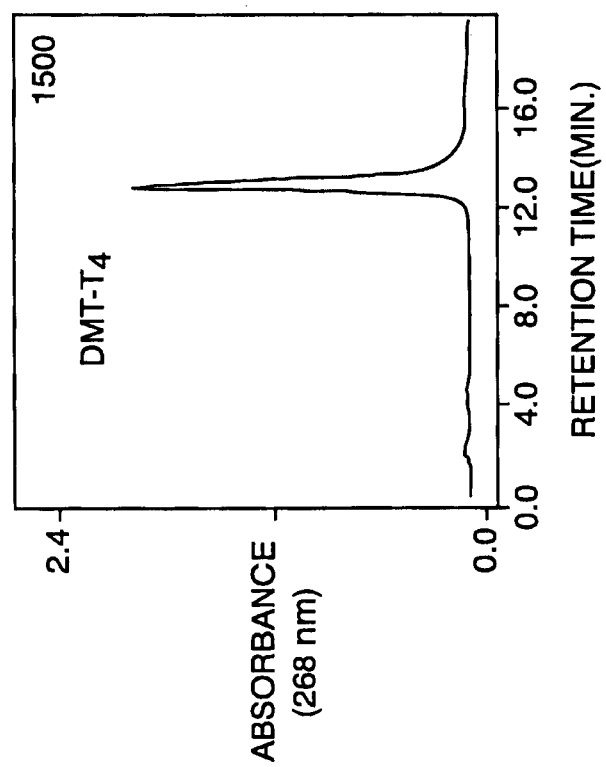
Figures 15C, 15D:
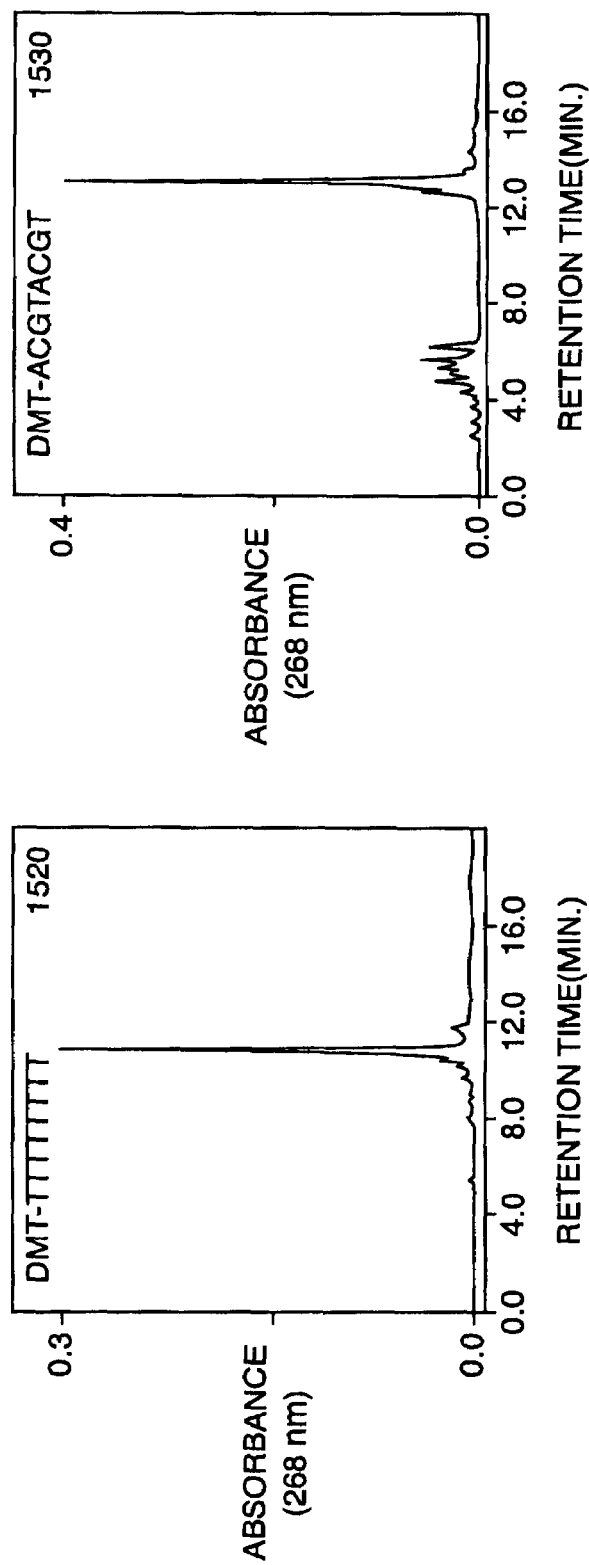

Synthesis of DMT-TTTT (1510 of FIG. 15), was carried out on a 0.2 µmol scale according to the protocol in Table 2. This is a direct adoption of the conventional phosphoramidite synthesis but with minor modifications at step 2. At this step, a PGA (0.4% of 50% triaryl sulfonium hexafluorophosphate in propylene carbonate) was added and the reaction column was irradiated with 365 nm light for 2 min. The column was extensively wash with solvents after the photo-deprotection reaction. Upon completion of the synthesis, the sequence was cleaved from CPG and deprotected using concentrated $NH_4OH$. The sample was examined using C18 reverse phase HPLC using a TEAA in $CH_3CN$ gradient. The HPLC profile of the crude product of DMT-TTTT synthesized using a PGA is shown (1510 of FIG. 15A). 1500 of FIG. 15 shows DMT-TTTT using the conventional TCA deprotection chemistry. 1520 and 1530 of FIG. 15B show HPLC profiles of the crude octanucleotides which was synthesized using the PGA approach.

TABLE 2

Protocol of Automated Oligonucleotide Synthesis (0.2 μmol)[1]

A. Using PGA

|  |  |  | Vol. (ml) | Time (sec) | Conc. (mM) | Amount Used (μmol) |
|---|---|---|---|---|---|---|
| 1 | detritylation[2] | 1% UVI-6974/ $CH_2Cl_2$ (v/v) | 1.20 | 180 | 100 | 114 |
| 2a | wash[3] | $CH_3CN$ | 2.40 | 200 |  |  |
| 2c | wash | $CH_2Cl_2$ | 2.00 | 50 |  |  |
| 3 | coupling | A. tetrazole/ $CH_3CN$ | 0.10 | 2 | 450 | 45 |
| 4 | coupling | A. tetrazole/ $CH_3CN$ | 0.10 | 2 | 450 | 45 |
| 5 | (simultaneous) | B. monomer/ $CH_3CN$ | 0.10 | 2 | 100 | 10 |
| 6 | coupling | B. tetrazole/ $CH_3CN$ | 0.10 | 63 | 450 | 45 |
| 7 | wash | $CH_3CN$ | 0.04 | 31 |  |  |
| 8 | wash | $CH_3CN$ | 0.66 | 17 |  |  |
| 9 | capping | A. acetic anhydride/ lutidine/THF | 0.15 | 4 | 10% | 147 |
| 10 | (simultaneous) | B. N-methyl-imidazole/THF | 0.15 | 4 | 10% | 183 |
| 11 | wash | $CH_3CN$ | 0.10 | 15 |  |  |
| 12 | wash | $CH_3CN$ | 0.27 | 7 |  |  |
| 13 | oxidation | $I_2$/THF/ pyridine/$H_2O$ | 0.29 | 7 | 0.02 | 6 |
| 14 | wash | $CH_3CN$ | 0.29 | 7 |  |  |
| 15 | capping | A. acetic anhydride/ lutidine/THF | 0.13 | 3 |  | 127 |
| 16 | (simultaneous) | B. N-methyl-imidazole/THF | 0.13 | 3 |  | 158 |
| 17 | wash | $CH_3CN$ | 0.57 | 15 |  |  |
|  | total (sec) |  |  | 612 |  |  |
|  | total (min) |  |  | 10.2 |  |  |

[1]Protocol is adopted from an Expedite 8909 synthesizer used for oligonucleotide synthesis using PGA deprotection.
[2]Highlighted steps for incorporation of the PGA reactions. Patterned light irradiation is applied at this step.
[3]Washing step is being optimized at this time to reduce the cycle time.

B. Using Conventional TCA

|  |  |  | Vol. (ml) | Time (sec) | Conc. (mM) | Amount Used (μmol) |
|---|---|---|---|---|---|---|
| 1 | detritylation | 3% TCA | 1.20 | 59 | 100 | 114 |
| 2 | wash | $CH_3CN$ | 1.00 | 20 |  |  |
| 3 | coupling | A. tetrazole/ $CH_3CN$ | 0.10 | 2 | 450 | 45 |
| 4 | coupling | A. tetrazole/ $CH_3CN$ | 0.10 | 2 | 450 | 45 |
| 5 | (simultaneous) | B. monomer/ $CH_3CN$ | 0.10 | 2 | 100 | 10 |
| 6 | coupling | B. tetrazole/ $CH_3CN$ | 0.10 | 63 | 450 | 45 |
| 7 | wash | $CH_3CN$ | 0.04 | 31 |  |  |
| 8 | wash | $CH_3CN$ | 0.66 | 17 |  |  |
| 9 | capping | A. acetic anhydride/ lutidine/THF | 0.15 | 4 | 10% | 147 |
| 10 | (simultaneous) | B. N-methyl-imidazole/THF | 0.15 | 4 | 10% | 183 |
| 11 | wash | $CH_3CN$ | 0.10 | 15 |  |  |
| 12 | wash | $CH_3CN$ | 0.27 | 7 |  |  |
| 13 | oxidation | $I_2$/THF/ pyridine/$H_2O$ | 0.29 | 7 | 0.02 | 6 |
| 14 | wash | $CH_3CN$ | 0.29 | 7 |  |  |
| 15 | capping | A. acetic anhydride/ lutidine/THF | 0.13 | 3 |  | 127 |
| 16 | (simultaneous) | B. N-methyl-imidazole/THF | 0.13 | 3 |  | 158 |
| 17 | wash | $CH_3CN$ | 0.57 | 15 |  |  |
|  | total (sec) |  |  | 261 |  |  |
|  | total (min) |  |  | 4.35 |  |  |

EXAMPLE V

Amino Acid Deprotection and Peptide Synthesis Using PGA

These experiments demonstrate efficient deprotection of the amino protection group using PGA in peptide synthesis.

Figure 16B:
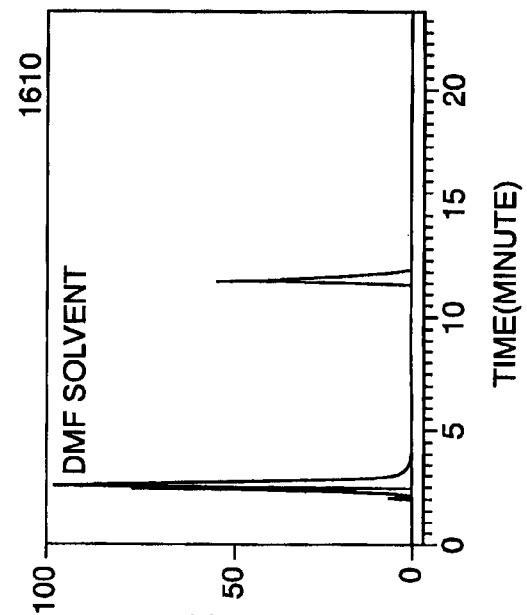
FIG. 16 shows the HPLC profiles of an amino acid deprotected using a photo-generated acid.
Figure 16A:
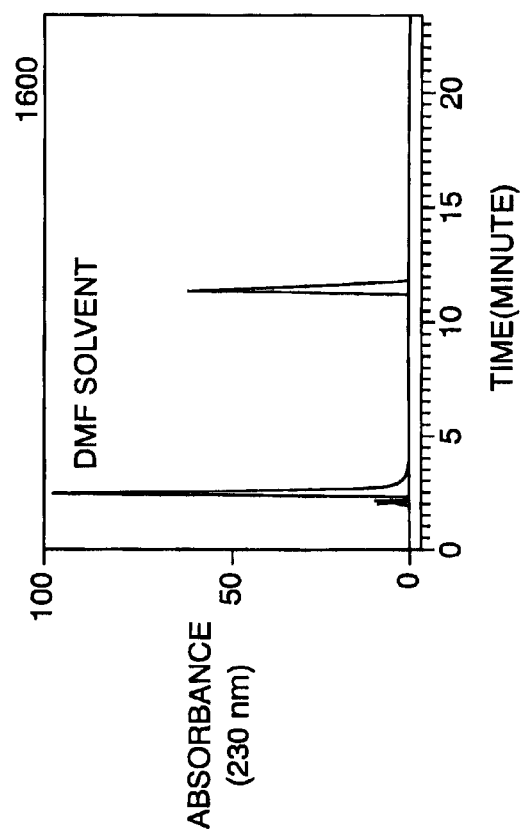

A sample of 10 mg (10 μmol) of HMPA resin (Nova Biochem, La Jolla, Calif.) containing t-Boc-Tyr was employed. Deprotection was performed in a $CH_2Cl_2$ solution containing a PGA (10% of 50% triaryl sulfonium hexafluoroantimonate in propylene carbonate) by irradiating the same solution at 365 nm for 15 min. The reaction was incubated for an additional 15 min and the resin was washed with $CH_2Cl_2$. The possible presence of residual amino groups was detected using ninhydrin color tests and the result was negative. The resin was then washed and the amino acid cleaved from the resin using NaOH (0.1 M in $CH_3OH$). 1610 of FIG. 16 shows the HPLC profile of the PGA deprotected Tyr. 1600 of FIG. 16 shows the HPLC profile of Tyr obtained using conventional trifluoroacetic acid (TFA) deprotection.

Synthesis of a pentapeptide, Leu-Phe-Gly-Gly-Tyr (SEQ ID NO:1), was accomplished using 100 mg of Merrifield resin. The PGA deprotection of the t-Boc group was performed and the resin was tested using ninhydrin until no color resulted. The coupling reaction was carried out using conditions well known to those skilled in the art. The PGA deprotection and coupling steps were repeated until the pentamer synthesis was completed. The sequence was cleaved from the resin and its HPLC compared well to that of the same sequence synthesized using conventional peptide chemistry.

EXAMPLE VI

Fabrication of Microwells

Formation of microwells using the fabrication methods of the present invention is demonstrated in this example. FIG.

Figure 17A:
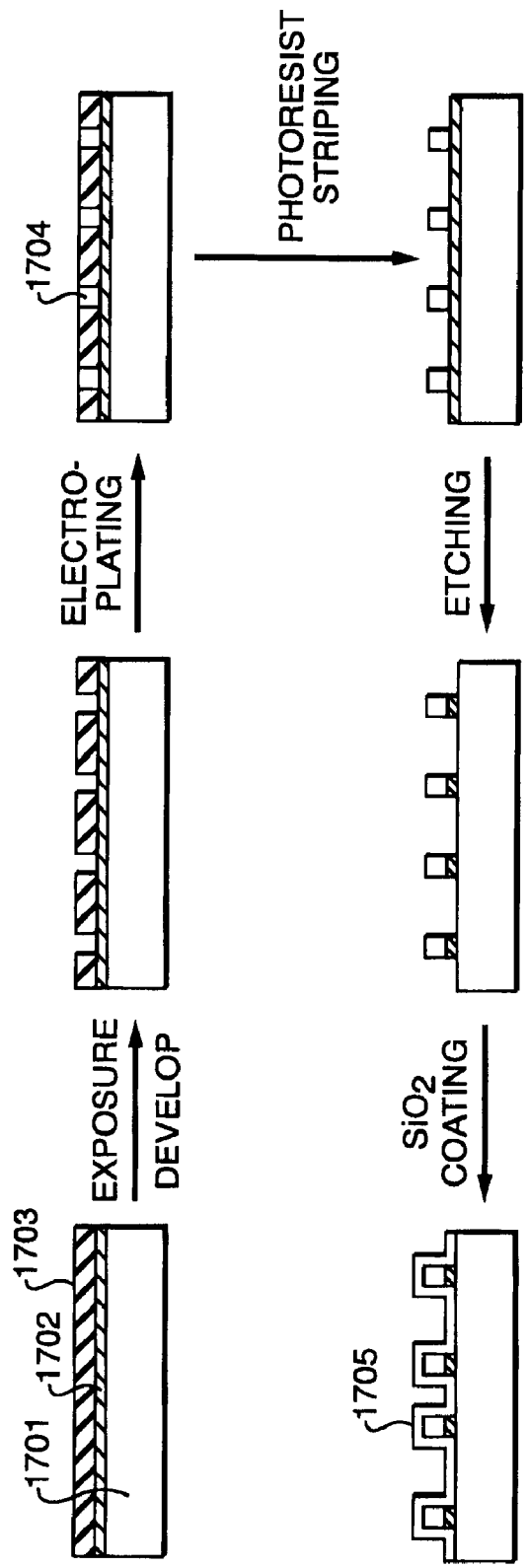
FIG. 17A illustrates a fabrication process for making microwells on a flat substrate.
Figure 17B:
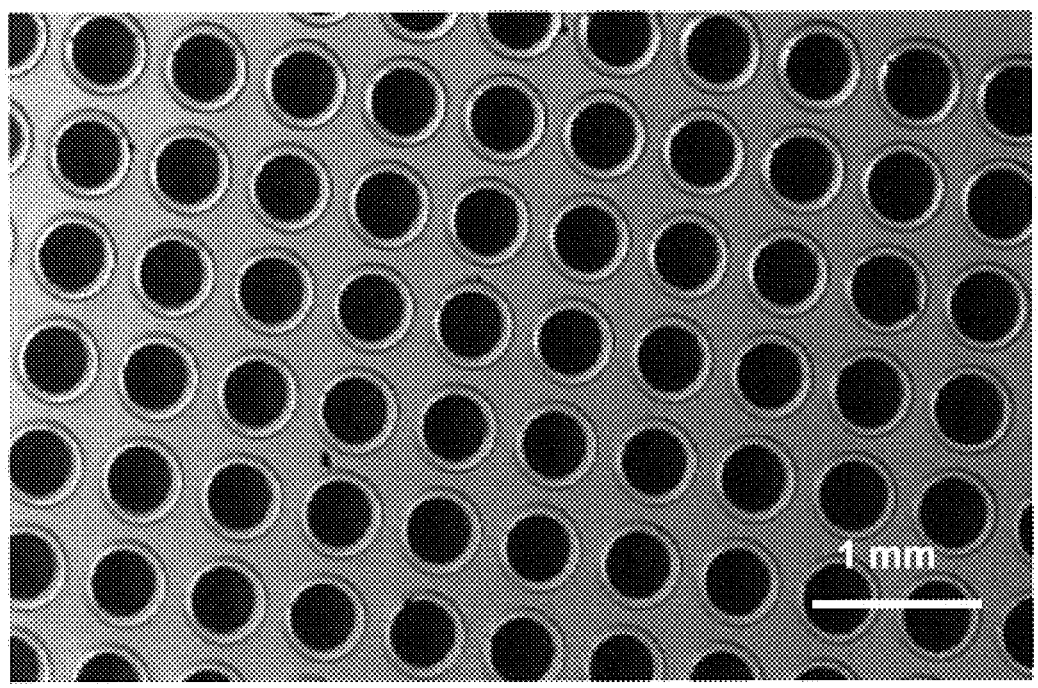
FIG. 17B is an enlarged photograph of microwells on a glass substrate.

17A schematically illustrates the fabrication procedure used. In the first fabrication step, a thin bimetal film 1702 of Cr/Cu 200/1000 Å thick was evaporated on a glass substrate 1701 in a sputtering evaporator. The bimetal film 1702 Cr provides good adhesion to the glass surface and Cu provides a good base for subsequent electroplating. The surface was then spin-coated with a positive photoresist 1703 of 18 μm thick. The photoresist film 1703 was then patterned using photolithography (exposure to UV light using a photomask aligner and development). Electroplating using a plating solution for a bright Ni was utilized to apply a plate a Ni film of 18 μm thick onto the exposed Cu surface resulting in microwell barriers 1704. The solution formula and plating conditions are as following. $NiSO_4.6H_2O$: 300 g/l, $NiCl_2.6H_2O$: 30-40 g/l, Boric Acid: 40 g/l, Sodium Saccharin: 2-5 g/l, Butynediol (2-Butyne-1,4-diol): 100 mg/l, Sodium lauryl sulfate: 50 ppm, pH: 3.0-4.2, Current density: 10 $A/dm^2$, Temperature: 50° C. The photoresist film 1703 was then stripped. Cu film was etched using a $HNO_3:H_3PO_4:CH_3COOH$. 0.5:50.0:49.5 (volume) solution and Cr film was etched using a HCl: $H_3PO_4:CH_3COOH$=5:45:50 (volume) solution activated by an aluminum stick. A spin-on glass film was then coated on to the sample surface to form a $SiO_2$ film 1705. FIG. 17B shows a photograph of the resulted microwell sample.

EXAMPLE VII

Solution Isolation Using Patterned Non-Wetting Films

Figure 18A:
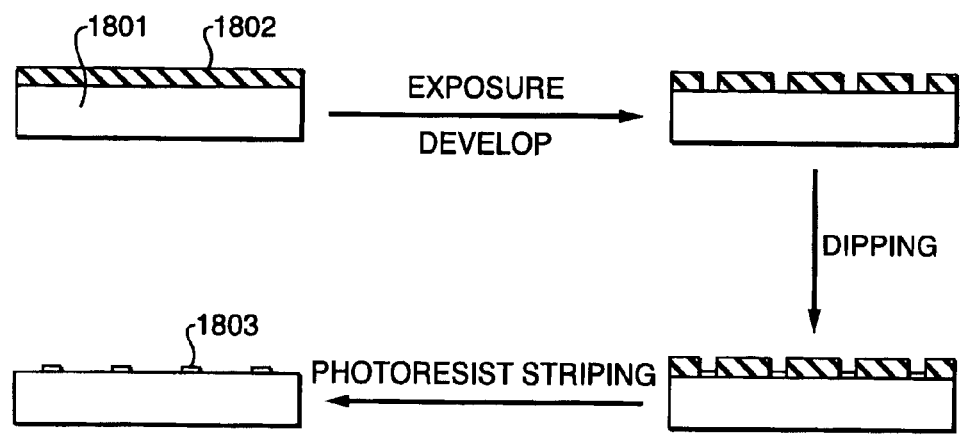
FIG. 18A illustrates a fabrication process for making a non-wetting-film pattern on a flat substrate.

This example illustrates that arrays of organic-solvent droplets were formed on a glass surface patterned with non-wetting films using the methods taught in the present invention. FIG. 18A schematically illustrates a fabrication procedure for coating a patterned non-wetting film on a glass substrate 1801. A glass substrate 1801 was thoroughly cleaned in a warm $H_2SO_4:H2O$=1:1 (volume) solution. The substrate 1801 was then spin-coated with a positive photoresist of about 2.7 μm thick. The photoresist film 1802 was exposed to UV light using a photomask aligner and developed. In this example, a photomask containing a matrix of circular dots were used and, therefore, the same pattern was formed in the photoresist film 1802. The patterned glass substrate was dipped into a 1 mM FDTS (1H, 1H, 2H, 2H-perfluorodecyltrichlorosiliane) anhydrous iso-octane solution in a dry box and soaked for at least 10 minutes. Then, the substrate was rinsed with iso-octane 2-3 times followed by a thorough water rinse. The photoresist was stripped and a FDTS film was left on the glass surface as a non-wetting film.

Figure 18B:
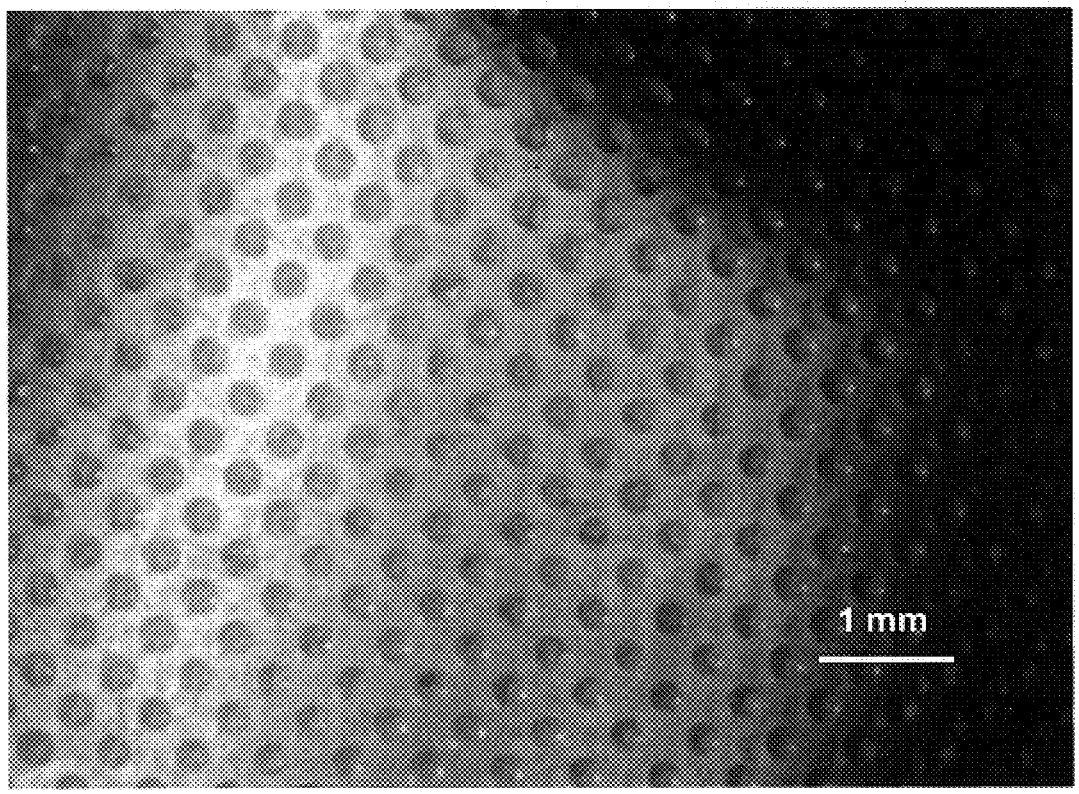
FIG. 18B is an enlarged photograph of methanol-droplets formed on a glass surface containing non-wetting film patterns.

Tests of wetting effects were performed in an enclosed cell to avoid evaporation of volatile solvents. During a test, the cell was filled with a testing solvent or solution and then drained. Tests were made on various organic/inorganic solvents and solutions including $CH_2Cl_2$, $CH_3CN$, $CH_3OH$, $CH_3CH_2OH$, $TCA/CH_2Cl_2$ solution, $I_2$/tetrahydrofuran-water-pyridine solution, and other solutions involved in oligonucleotide synthesis. Formation of droplet arrays was observed for each testing solvent/solution FIG. 18B shows a photograph of methanol droplet array formed on a non-wetting film patterned glass plate.

EXAMPLE VIII

Array Synthesis on a Patterned Glass Substrate Using PGA

These experiments demonstrate the use of the method and instrument of the present invention in making molecular microarray chips.

Figure 19:
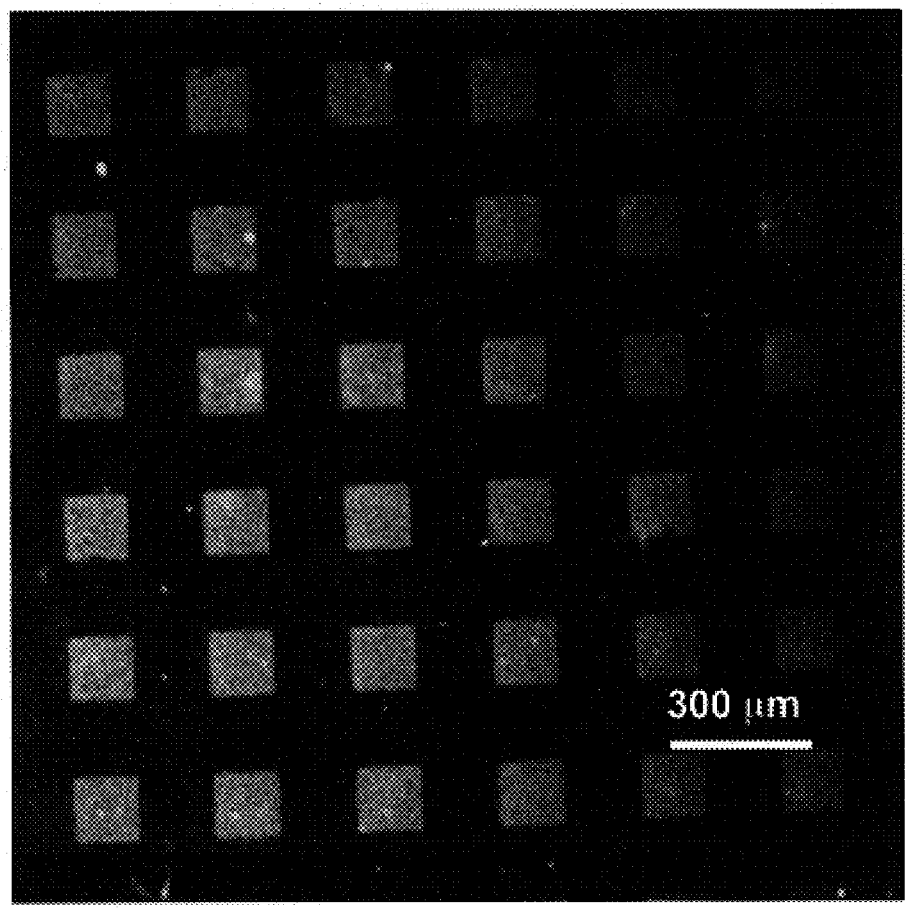
FIG. 19 is a fluorescence image of fluorescein tagged thymine grown on a non-wetting film patterned glass plate.

Fabricated glass substrates containing isolated reaction wells at specified areas as described in Example VI were employed. The glass plates were derivatized with linker molecules (10% N-(3-triethoxysilylpropyl)-4-hydroxylbutyramide in ethanol) containing free OH groups. Synthesis on the glass substrate was performed using a reactor and a digital light projector as described in this specification and a DNA synthesizer (Perspective). Oligonucleotide synthesis was accomplished according to the protocol shown in Table 2. The glass surface was first contacted with DMT-T phosphoramidite to couple the first residue. The sequences were treated, in subsequent steps, with capping and oxidation reagents and washed with $CH_3CN$ before and after each step of the reactions. The glass plate was then treated with a PGA (0.4% of 50% triaryl sulfonium hexafluorophosphate in $CH_2Cl_2$) delivered by the synthesizer and exposed to computer generated patterned light irradiation (30 s) from a collimated light source at 365 nm and 3 mw of light source intensity, (Stanford, Calif.). The surface was then extensively washed with $CH_3CN$. In the light exposed areas, free hydroxyl groups were generated. After oxidation and wash steps, the surface was contacted by fluorescein-labeled phosphoramidite monomers in a second coupling step. The molecular arrays synthesized were treated with NaOH aqueous solution (0.1 M). The array contains fluorescence labeled dimers were visualized under a fluoromicroscope (Bio-Rad, Richmond, Calif.). The results of which are shown in FIG. 19.

---

We claim:

1. A method for parallel synthesis of an array of selected multimers on a substrate comprising fluidly isolated reaction sites containing one or more protected initiation moieties, the method comprising:
   (a) selectively irradiating, using a spatial optical modulator comprising a digital micromirror device, fluidly isolated reaction sites to generate deprotected initiation moieties at the irradiated fluidly isolated reaction sites; wherein the deprotected initiation moieties are generated by:
      (i) contacting the substrate with a liquid solution comprising one or more photo-reagent precursors, such that the liquid solution is in contact with the initiation moieties; and
      (ii) selectively irradiating fluidly isolated reaction sites to produce one or more photo-generated reagents, wherein the photo-generated reagents are effective to deprotect the initiation moieties at the irradiated fluidly isolated reaction sites;
   (b) coupling one or more monomers to the deprotected initiation moieties to generate new protected initiation moieties; and
   (c) repeating steps (a)-(b) until the array of selected multimers has been synthesized; wherein the coupling reactions to synthesize the array of selected multimers occur with a yield of 98% or greater.

2. The method of claim 1, wherein the selected multimers are DNA.

3. The method of claim 2, wherein the DNA is selected from the group consisting of nucleotide phosphoramidites and analogs thereof.

4. The method of claim 1, wherein the selected multimers are oligonucleotides.

5. The method of claim 1, wherein the selected multimers are RNA.

6. The method of claim 1, wherein the selected multimers are DNA/RNA hybrids.

7. The method of claim 1, wherein the selected multimers are peptides.

8. The method of claim 1, wherein the selected multimers are carbohydrates.

9. The method of claim 1, wherein the photo-reagent precursors are selected from the group consisting of acid precursors and base precursors.

10. The method of claim 1, wherein the monomer comprises an unprotected reactive site and a protected reactive site.

11. The method of claim 1, wherein the protected initiation moieties are protected by an acid-labile group.

12. The method of claim 1, wherein the protected initiation moieties comprise linker molecules, wherein each of the linker molecules comprise a reactive functional group protected by an acid-labile group.

13. A method for generating a photogenerated reaction in solution on a substrate comprising:
   a) generating a light beam using an optical device system comprising a light source and a computer-controlled spatial optical modulator comprising a digital micromirror device; and
   b) redirecting the light beam using the spatial optical modulator comprising a digital micromirror device to a fluidly isolated reaction site on said substrate under conditions such that a photogenerated reaction takes place, wherein said photogenerated reaction comprises contacting said substrate with a liquid solution comprising one or more photo-reagent precursors, said precursors selected from the group consisting of acid precursors and base precursors, such that the liquid solution is in contact with initiation moieties on said substrate and selectively irradiating fluidly isolated reaction sites with said micromirror device to produce one or more photo-generated reagents, wherein said photo-generated reagents deprotect initiation moieties at the irradiated, fluidly isolated reaction sites.

14. The method of claim 13, wherein the digital micromirror device comprises a plurality of micromirrors.

15. The device of claim 14, wherein the micromirrors are individual rocking mirrors.

16. A method for parallel synthesis of an array of selected multimers on a substrate comprising isolated reaction sites containing one or more protected initiation moieties, the method comprising:

(a) selectively irradiating, using a spatial optical modulator comprising a digital micromirror device, fluidly isolated reaction sites to generate deprotected initiation moieties at the irradiated isolated reaction sites, wherein generating said deprotected initiation moieties comprises:
   (i) contacting the substrate with a liquid solution comprising one or more photo-reagent precursors, said precursors selected from the group consisting of acid precursors and base precursors, such that the liquid solution is in contact with the initiation moieties; and
   (ii) selectively irradiating fluidly isolated reaction sites to produce one or more photo-generated reagents, wherein the photo-generated reagents deprotect the initiation moieties at the irradiated, fluidly isolated reaction sites;

(b) coupling one or more monomers to the deprotected initiation moieties to generate new protected initiation moieties; and (c) repeating steps (a)-(b) until the array of selected multimers has been synthesized; wherein the coupling reactions to synthesize the array of selected multimers occur with a yield of 98% or greater.

17. The method of claim 16, wherein the selected multimers are DNA.

18. The method of claim 17, wherein the DNA is selected from the group consisting of nucleotide phosphoramidites and analogs thereof.

19. The method of claim 16, wherein the selected multimers are oligonucleotides.

20. The method of claim 16, wherein the monomer comprises an unprotected reactive site and a protected reactive site.

21. The method of claim 16, wherein the protected initiation moieties are protected by an acid-labile group.

22. The method of claim 16, wherein the protected initiation moieties comprise linker molecules, wherein each of the linker molecules comprise a reactive functional group protected by an acid-labile group.

* * * * *

SEQUENCE LISTING

<160> NUMBER OF SEQ ID NOS: 5

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Leu Phe Gly Gly Tyr
1               5

```
<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Val Asp Ala Glu
1

<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Thr Tyr Ala Gln
1

<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Ile Tyr Ser Glu
1

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Ala Asp Ser Gln
1
```